United States Patent
Yamago et al.

(10) Patent No.: US 7,847,043 B2
(45) Date of Patent: Dec. 7, 2010

(54) ORGANIC BISMUTH COMPOUND, METHOD FOR PRODUCING SAME, LIVING RADICAL POLYMERIZATION INITIATOR, METHOD FOR PRODUCING POLYMER USING SAME, AND POLYMER

(75) Inventors: Shigeru Yamago, Osaka (JP); Takashi Kameshima, Tokushima (JP); Kazuhiro Kawano, Tokushima (JP); Osamu Ito, Tokushima (JP); Emiko Daimon, Tokushima (JP); Ken Shu, Tokushima (JP); Kunihiko Sugoh, Tokushima (JP)

(73) Assignees: Otsuka Chemical Co., Ltd., Osaka (JP); Japan Science and Technology Agency, Saitama (JP)

(*) Notice: Subject to any disclaimer, the term of this patent is extended or adjusted under 35 U.S.C. 154(b) by 781 days.

(21) Appl. No.: 11/792,299

(22) PCT Filed: Dec. 9, 2005

(86) PCT No.: PCT/JP2005/023093

§ 371 (c)(1),
(2), (4) Date: Jun. 5, 2007

(87) PCT Pub. No.: WO2006/062255

PCT Pub. Date: Jun. 15, 2006

(65) Prior Publication Data

US 2007/0265404 A1 Nov. 15, 2007

(30) Foreign Application Priority Data

Dec. 10, 2004 (JP) .............................. 2004-358238
Sep. 2, 2005 (JP) .............................. 2005-255327

(51) Int. Cl.
*C08F 4/20* (2006.01)
*C08F 9/94* (2006.01)

(52) U.S. Cl. .......................... 526/190; 546/4; 548/403; 549/209; 549/3; 556/70

(58) Field of Classification Search ................. 526/190; 546/4; 548/403; 549/209, 3; 556/70
See application file for complete search history.

(56) References Cited

U.S. PATENT DOCUMENTS

2005/0245714 A1 11/2005 Yamago et al.

FOREIGN PATENT DOCUMENTS

JP 63-273610 11/1988

OTHER PUBLICATIONS

Ashe et al., Organometallics 1983 2 1859-1866.*
Arthur J. Ashe, III, et al., "Preparation and Properties of Dibismuthines", Organometallics, vol. 2, No. 12, pp. 1859-1866 (1983).

* cited by examiner

*Primary Examiner*—Robert D. Harlan
(74) *Attorney, Agent, or Firm*—Wenderoth, Lind & Ponack, LLP.

(57) ABSTRACT

An organobismuth compound represented by the formula (1)

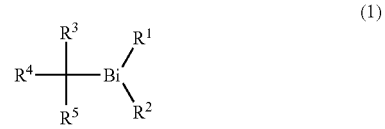

(1)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, amido, oxycarbonyl or cyano.

37 Claims, No Drawings

ORGANIC BISMUTH COMPOUND, METHOD FOR PRODUCING SAME, LIVING RADICAL POLYMERIZATION INITIATOR, METHOD FOR PRODUCING POLYMER USING SAME, AND POLYMER

TECHNICAL FIELD

The present invention relates to organobismuth compounds and a process for preparing the same. More particularly, the invention relates to living radical polymerization initiators of the organobismuth type, a process for preparing living radical polymers using the initiator and living radical polymers. The present invention also relates to a process for preparing a random copolymer and the random copolymer, a process for preparing a block copolymer and the block copolymer, and these macro living radical polymerization initiators and polymers.

Further, the polymer of the present invention is suitable for use as a resist material and the like usable for preparing a semiconductor device.

BACKGROUND ART

Living radical polymerization is a polymerization process which is adapted for precision control of molecular structures while ensuring convenience and universal usefulness of radical polymerization, and is powerful means for preparing novel high polymer materials. The present inventors have reported, as an example, a living radical polymerization using an organotellurium compound as an initiator (for example, patent literature 1).

[patent literature 1] WO 2004/14848

The process of patent literature 1 makes it possible to control molecular weights and molecular weight distributions, but utilizes an organotellurium initiator and has no disclosure about organobismuth compounds of the present invention. Further, organobismuth compounds are excellent in safety than organotellurium compounds.

An object of the present invention is to provide a process for preparing living radical polymers and the polymers, which makes possible precision control of molecular weights and molecular weight distributions (PD=Mw/Mn), by polymerizing a vinyl monomer using an organobismuth compound.

An object of the present invention is to provide a process for preparing living radical polymers and the polymers, which makes possible precision control of molecular weights and molecular weight distributions (PD=Mw/Mn) under mild conditions, in short period of time and in high yield for preparing the compound, a process for producing a polymer with use of the compound, and the polymer.

DISCLOSURE OF THE INVENTION

1. An organobismuth compound represented by the formula (1)

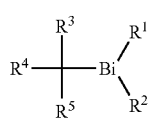

(1)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, amido, oxycarbonyl or cyano.

2. A process for preparing an organobismuth compound of the formula (1) comprising reacting a compound of the formula (3), and a compound of the formula (4) or (5)

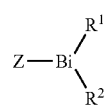

(3)

(wherein $R^1$ and $R^2$ are as defined above, and Z is a halogen atom or alkali metal)

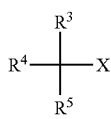

(4)

(wherein $R^3$, $R^4$ and $R^5$ are as defined above, and X is a halogen atom)

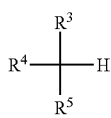

(5)

(wherein $R^3$, $R^4$ and $R^5$ are as defined above).

3. A living radical polymerization initiator of the formula (2)

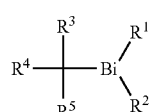

(2)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^6$ is aryl, substituted aryl, an aromatic heterocyclic group, acyl, amido, oxycarbonyl or cyano.

4. A process for producing a living radical polymer wherein a vinyl monomer is polymerized with use of a living radical polymerization initiator of the formula (2).

5. A process for producing a living radical polymer wherein a vinyl monomer is polymerized with use of a living radical polymerization initiator of the formula (2) and an azo type polymerization initiator.

6. A process for producing a random copolymer wherein at least two vinyl monomers are polymerized with use of a living radical polymerization initiator of the formula (2), or this initiator and an azo type polymerization initiator.

7. A macro living radical polymerization initiator which is obtainable by subjecting a vinyl monomer to polymerization with use of a living radical polymerization initiator of the formula (2), or this initiator and an azo type polymerization initiator.

8. A process for producing a living radical polymer wherein a vinyl monomer is polymerized with use of a living radical polymerization initiator of the formula (2), at least one compound selected from ditelluride compound, distibine compound and dibismuthine compound, and as required an azo type polymerization initiator.

9. A process for producing a resin containing an acid-dissociable group wherein a vinyl monomer is polymerized with use of one of the following (a) to (d), (a) a living radical polymerization initiator of the formula (2), (b) a mixture of a living radical polymerization initiator of the formula (2), and an azo type polymerization initiator, (c) a mixture of a living radical polymerization initiator of the formula (2), and at least one compound selected from ditelluride compound, distibine compound and dibismuthine compound, and (d) a mixture of a living radical polymerization initiator of the formula (2), an azo type polymerization initiator, and at least one compound selected from ditelluride compound, distibine compound and dibismuthine compound.

10. A radiation-sensitive resin composition comprising a resin containing an acid-dissociable group, and a radiation-sensitive acid producing agent.

The organobismuth compounds of the present invention are represented by the formula (1)

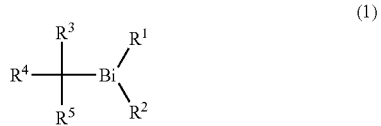

(1)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, amido, oxycarbonyl or cyano.

Examples of groups represented by $R^1$ and $R^2$ are as follows.

Examples of $C_1$-$C_8$ alkyl groups usable are straight-chain, branched chain or cyclic alkyl groups having 1 to 8 carbon atoms, such as methyl, ethyl, n-propyl, isopropyl, cyclopropyl, n-butyl, sec-butyl, tert-butyl, cyclobutyl, n-pentyl, n-hexyl, n-heptyl and n-octyl. Preferable alkyl groups are straight-chain or branched chain alkyl groups having 1 to 4 carbon atoms. Methyl, ethyl or n-butyl is more preferable.

Examples of aryl groups are phenyl and naphthyl. Preferable is phenyl. Examples of substituted aryl groups are phenyl having a substituent and naphthyl having a substituent.

Examples of substituents of aryl groups having a substituent are a halogen atom, hydroxyl, alkoxyl, amino, nitro, cyano, carbonyl-containing groups represented by —$COR^a$ ($R^a$=$C_1$-$C_8$ alkyl, aryl, $C_1$-$C_8$ alkoxyl or aryloxy), sulfonyl, trifluoromethyl, etc. Preferable aryl group having a substituent is trifluoromethyl-substituted phenyl. Preferably such substituted groups have one or two substituents at the para-position or ortho-position. Examples of aromatic heterocyclic groups are pyridyl, pyrrol, furyl and thienyl.

Examples of groups represented by $R^3$ and $R^4$ are as follows.

Examples of $C_1$-$C_8$ alkyl groups usable are the same as the alkyl groups represented by $R^1$ and given above.

Examples of groups represented by $R^5$ are as follows.

Examples of aryl, substituted aryl, aromatic heterocyclic groups usable are the same as those groups represented by $R^1$ and given above.

Examples of acyl groups are formyl, acetyl and benzoyl.

Examples of amido groups are acetamido, malonamido, succinamido, maleamido, benzamido, 2-furamido and like carbonamido, thioacetamido, hexanedithioamido, thiobenzamido methanethiosulfonamido and like thioamido, selenoacetamido, hexanediselenoamido, selenobenzamido methaneselenosulfonamido and like selenoamido, N-methylacetamido, benzanilido, cyclohexanecarboxyanilido, 2,4'-dichloroacetanilido and like N-substituted amido.

Examples of preferred oxycarbonyl groups are those represented by —$COOR^b$ ($R^b$=H, $C_1$-$C_8$ alkyl or aryl) such as carboxyl, methoxycarbonyl, ethoxycarbonyl, propoxycarbonyl, n-butoxycarbonyl, sec-butoxycarbonyl, tert-butoxycarbonyl, n-pentoxycarbonyl and phenoxycabonyl. Methoxycarbonyl and ethoxycarbonyl are more preferable oxycarbonyl groups.

Examples of preferred groups represented by $R^5$ are aryl, substituted aryl, oxycarbonyl and cyano. The aryl group is preferably phenyl. Examples of preferred substituted aryl groups are phenyl substituted with a halogen atom and phenyl substituted with trifluoromethyl. When the substituent is a halogen, the phenyl is substituted with preferably one to five halogen atoms. In the case of alkoxyl or trifluoromethyl, preferably one or two substituents are present. When having one substituent, the group is substituted preferably at the para- or ortho-position. When the group has two substituents, the meta-positions are preferred. Examples of preferred oxycarbonyl groups are methoxycarbonyl and ethoxycarbonyl.

Examples of preferred organobismuth compounds represented by the formula (1) are compounds wherein $R^1$ and $R^2$ are $C_1$-$C_4$ alkyl, $R^3$ and $R^4$ are each a hydrogen atom or $C_1$-$C_4$ alkyl, and $R^5$ is aryl, substituted aryl or oxycarbonyl. Especially preferable organobismuth compounds are those wherein $R^1$ and $R^2$ are $C_1$-$C_4$ alkyl, $R^3$ and $R^4$ are each a hydrogen atom or $C_1$-$C_4$ alkyl, and $R^5$ is phenyl, substituted phenyl, methoxycarbonyl or ethoxycarbonyl.

Examples of organobismuth compounds represented by the formula (1) are as follows.

(Dimethylbismuthanyl-methyl)benzene, (dimethylbismuthanyl-methyl)naphthalene, 1-chloro-4-(dimethylbismuthanyl-methyl)benzene, 1-hydroxy-4-(dimethylbismuthanyl-methyl)benzene, 1-methoxy-4-(dimethylbismuthanyl-methyl)benzene, 1-amino-4-(dimethylbismuthanyl-methyl)benzene, 1-nitro-4-(dimethylbismuthanyl-methyl)benzene, 1-cyano-4-(dimethylbismuthanyl-methyl)benzene, 1-methylcarbonyl-4-(dimethylbismuthanyl-methyl)benzene, 1-phenylcarbonyl-4-(dimethylbismuthanyl-methyl)benzene, 1-methoxycarbonyl-4-(dimethylbismuthanyl-methyl)benzene, 1-phenoxycarbonyl-4-(dimethylbismuthanyl-methyl)benzene, 1-sulfonyl-4-(dimethylbismuthanyl-methyl)benzene, 1-trifluoromethyl-4-(dimethylbismuthanyl-methyl)benzene, 3,5-bis-trifluoromethyl-1-(dimethylbismuthanyl-methyl)-benzene, 1,2,3,4,5-pentafluoro-6-(dimethylbismuthanyl-methyl)benzene, 2-(dimethylbismuthanyl-methyl)pyridine, 1-(dimethylbismuthanyl-methyl)-1H-pyrrole, 2-(dimethylbismuthanyl-methyl)furan, 2-(dimethylbismuthanyl-methyl)thiophene, (dimethylbismuthanyl)acetaldehyde, 1-(dimethylbismuthanyl)propane-2-one, 2-(dimethylbismuthanyl)-1-phenyl-ethanone, (dimethylbismuthanyl)acetate, methyl dimethylbismuthanyl-acetate, ethyl dimethylbismuthanyl-acetate, n-propyl dimethylbismuthanyl-acetate, n-butyl dimethylbismuthanyl-acetate, phenyl dimethylbismuthanyl-acetate, (dimethylbismuthanyl)acetonitrile, (1-dimethylbismuthanyl-ethyl)benzene, (1-dimethylbismuthanyl-ethyl)naphthalene, 1-chloro-4-(1-dimethylbismuthanyl-ethyl)benzene, 1-hydroxy-4-(1-dimethylbismuthanyl-ethyl)benzene, 1-methoxy-4-(1-dimethylbismuthanyl-ethyl)benzene, 1-amino-4-(1-dimethylbismuthanyl-ethyl)benzene, 1-nitro-4-(1-dimethylbismuthanyl-ethyl)benzene, 1-cyano-4-(1-dimethylbismuthanyl-ethyl)benzene, 1-methylcarbonyl-4-(1-dimethylbismuthanyl-ethyl)benzene, 1-phenylcarbonyl-4-(1-dimethylbismuthanyl-ethyl)benzene, 1-methoxycarbonyl-4-(1-dimethylbismuthanyl-ethyl)benzene, 1-phenoxycarbonyl-4-(1-dimethylbismuthanyl-ethyl)benzene, 1-sulfonyl-4-(1-dimethylbismuthanyl-ethyl)benzene, 1-trifluoromethyl-4-(1-dimethylbismuthanyl-ethyl)benzene, 3,5-bis-trifluoromethyl-1-(1-dimethylbismuthanyl-ethyl)-benzene, 1,2,3,4,5-pentafluoro-6-(1-dimethylbismuthanyl-ethyl)benzene, 2-(1-dimethylbismuthanyl-ethyl)pyridine, 1-(1-dimethylbismuthanyl-ethyl)-1H-pyrrole, 2-(1-dimethylbismuthanyl-ethyl)furan, 2-(1-dimethylbismuthanyl-ethyl)thiophene, 2-dimethylbismuthanyl-propionaldehyde, 3-dimethylbismuthanyl-butane-2-one, 2-dimethylbismuthanyl-1-phenyl-propane-1-one, 2-dimethylbismuthanyl-propionate, methyl 2-dimethylbismuthanyl-propionate, ethyl 2-dimethylbismuthanyl-propionate, n-propyl 2-dimethylbismuthanyl-propionate, n-butyl 2-dimethylbismuthanyl-propionate, phenyl 2-dimethylbismuthanyl-propionate, 2-dimethylbismuthanyl-propionitrile, (2-dimethylbismuthanyl-propyl)benzene, (2-dimethylbismuthanyl-propyl)naphthalene, 1-chloro-4-(1-dimethylbismuthanyl-1-methyl-ethyl)benzene, 1-hydroxy-4-(1-dimethylbismuthanyl-1-methyl-ethyl)benzene, 1-methoxy-4-(1-dimethylbismuthanyl-1-methyl-ethyl)benzene, 1-amino-4-(1-dimethylbismuthanyl-1-methyl-ethyl)benzene, 1-nitro-4-(1-dimethylbismuthanyl-1-methyl-ethyl)benzene, 1-cyano-4-(1-dimethylbismuthanyl-1-methyl-ethyl)benzene, 1-methylcarbonyl-4-(1-dimethylbismuthanyl-1-methyl-ethyl)benzene, 1-phenylcarbonyl-4-(1-dimethylbismuthanyl-1-methyl-ethyl)benzene, 1-methoxycarbonyl-4-(1-dimethylbismuthanyl-1-methyl-ethyl)benzene, 1-phenoxycarbonyl-4-(1-dimethylbismuthanyl-1-methyl-ethyl)benzene, 1-sulfonyl-4-(1-dimethylbismuthanyl-1-methyl-ethyl)benzene, 1-trifluoromethyl-4-(1-dimethylbismuthanyl-1-methyl-ethyl)benzene, 3,5-bis-trifluoromethyl-1-(1-dimethylbismuthanyl-1-methyl-ethyl)benzene, 1,2,3,4,5-pentafluoro-6-(1-dimethylbismuthanyl-1-methyl-ethyl)benzene, 2-(1-dimethylbismuthanyl-1-methyl-ethyl)pyridine, 1-(1-dimethylbismuthanyl-1-methyl-ethyl)-1H-pyrrole, 2-(1-dimethylbismuthanyl-1-methyl-ethyl)furan, 2-(1-dimethylbismuthanyl-1-methyl-ethyl)thiophene, 2-dimethylbismuthanyl-2-methyl-propionaldehyde, 3-dimethylbismuthanyl-3-methyl-butane-2-one, 2-dimethylbismuthanyl-2-methyl-1-phenyl-propane-1-one, 2-dimethylbismuthanyl-2-methyl-propionate, methyl 2-dimethylbismuthanyl-2-methyl-propionate, ethyl 2-dimethylbismuthanyl-2-methyl-propionate, n-propyl 2-dimethylbismuthanyl-2-methyl-propionate, n-butyl 2-dimethylbismuthanyl-2-methyl-propionate, phenyl 2-dimethylbismuthanyl-2-methyl-propionate, 2-dimethylbismuthanyl-2-methyl-propionitrile, etc.

The above compounds also include all compounds having diethylbismuthanyl, di-n-propylbismuthanyl or diphenylbismuthanyl, as changed from the portion of dimethylbismuthanyl.

The organobismuth compound represented by the formula (1) can be prepared by reacting a compound of the formula (3) and, a compound of the formula (4) or a compound of the formula (5)

(wherein $R^1$ and $R^2$ are defined above, and Z is a halogen atom or alkali metal)

(wherein $R^3$, $R^4$ and $R^5$ are defined above, and X is a halogen atom)

(wherein $R^3$, $R^4$ and $R^5$ are defined above).

Examples of compounds represented by the formula (3) are as follows

Examples of groups represented by $R^1$ and $R^2$ are as given above.

Examples of groups represented by Z are halogen atom such as fluorine, chlorine, bromine or iodine or alkali metal such as sodium, potassium or lithium. Preferable are chlorine, bromine, sodium and lithium.

The compound (3) can be prepared, for example, by disproportionation reaction of trialkylbismutane and bismuth trihalide disclosed in Chem. Rev. 1982, vol. 82, page 15.

Examples of compound (3) are dimethylbismuthanyl bromide, diethylbismuthanyl bromide, di-n-butylbismuthanyl bromide, diphenylbismuthanyl bromide, dimethylbismuthanyl sodium, diethylbismuthanyl sodium, di-n-butylbismuthanyl sodium and diphenylbismuthanyl sodium. The above compounds also include all compounds having chloride or iodide, as changed from the portion of bromide. Further, the above compounds also include all compounds having potassium or lithium, as changed from the portion of sodium.

Examples of compounds represented by the formula (4) are as follows

Examples of groups represented by $R^3$, $R^4$ and $R^5$ are as given above.

Examples of groups represented by X can be a halogen atom such as fluorine, chlorine, bromine or iodine. Chlorine and bromine are preferable.

Examples of compounds (4) usable are benzyl chloride, benzyl bromide, 1-chloromethylnaphthalene, 1-bromomethylnaphthalene, p-chlorobenzyl chloride, p-hydroxybenzyl chloride, p-methoxybenzyl chloride, p-aminobenzyl chloride, p-nitrobenzyl chloride, p-cyanobenzyl chloride, p-methylcarbonylbenzyl chloride, phenylcarbonylbenzyl chloride, p-methoxycarbonylbenzyl chloride, p-phenoxycarbonylbenzyl chloride, p-sulfonylbenzyl chloride, p-trifluoromethylbenzyl chloride, 3,5-bis-trifluoromethylbenzyl chloride, 1,2,3,4,5-pentafluoromethylbenzyl chloride, 2-(chloromethyl)pyridine, 2-(bromomethyl)pyridine, 1-(chloromethyl)-1H-pyrrole, 2-(chloromethyl)furan, 2-(bromomethyl)furan, 2-(chloromethyl)thiophene, 2-(bromomethyl)thiophene, chloroacetaldehyde, bromoacetaldehyde, 1-chloro-propane-2-one, 1-bromo-propane-2-one, 2-chloro-1-phenyl-ethanone, 2-chloro-1-phenyl-ethanone, chloroacetic acid, bromoacetic acid, methyl 2-chloroacetate, methyl 2-bromoacetate, ethyl 2-chloroacetate, ethyl 2-bromoacetate, n-propyl 2-chloroacetate, n-propyl 2-bromoacetate, n-butyl 2-chloroacetate, n-butyl 2-bromoacetate, phenyl 2-chloroacetate, phenyl 2-bromoacetate, 2-chloroacetonitrile, 2-bromoacetonitrile, (1-chloroethyl)benzene, (1-bromoethyl)benzene, (1-chloroethyl)naphthalene, (1-bromoethyl)naphthalene, 1-chloro-4-(1-chloroethyl)benzene, 1-hydroxy-4-(1-chloroethyl)benzene, 1-methoxy-4-(1-chloroethyl)benzene, 1-amino-4-(1-chloroethyl)benzene, 1-nitro-4-(1-chloroethyl)benzene, 1-cyano-4-(1-chloroethyl)benzene, 1-methylcarbonyl-4-(1-chloroethyl)benzene, 1-phenylcarbonyl-4-(1-chloroethyl)benzene, 1-methoxycarbonyl-4-(1-chloroethyl)benzene, 1-phenoxycarbonyl-4-(1-chloroethyl)benzene, 1-sulfonyl-4-(1-chloroethyl)benzene, 1-trifluoromethyl-4-(1-chloroethyl)benzene, 3,5-bis-trifluoromethyl-1-(1-chloroethyl)benzene, 1,2,3,4,5-pentafluoro-6-(1-chloroethyl)benzene, 2-(1-chloroethyl)pyridine, 2-(1-bromoethyl)pyridine, 1-(1-chloroethyl)-1H-pyrrole, 1-(1-bromoethyl)-1H-pyrrole, 2-(1-chloroethyl)furan, 2-(1-bromoethyl)furan, 2-(1-chloroethyl)thiophene, 2-(1-bromoethyl)thiophene, 2-chloro-propionaldehyde, 2-bromopropionaldehyde, 3-chloro-butane-2-one, 3-bromo-butane-2-one, 2-chloro-1-phenyl-propan-1-one, 2-bromo-1-phenyl-propan-1-one, 2-chloropropionic acid, 2-bromopropionic acid, methyl 2-chloropropionate, methyl 2-bromopropionate, ethyl 2-chloropropionate, ethyl 2-bromopropionate, propyl 2-chloropropionate, propyl 2-bromopropionate, n-butyl 2-chloropropionate, n-butyl 2-bromopropionate, 2-chloropropionitrile, 2-bromopropionitrile, (2-chloropropyl)benzene, (2-bromopropyl)benzene, (2-chloropropyl)naphthalene, (2-chloropropyl)naphthalene, 1-chloro-4-(2-chloropropyl)benzene, 1-hydroxy-4-(2-chloropropyl)benzene, 1-methoxy-4-(2-chloropropyl)benzene, 1-amino-4-(2-chloropropyl)benzene, 1-nitro-4-(2-chloropropyl)benzene, 1-cyano-4-(2-chloropropyl)benzene, 1-methylcarbonyl-4-(2-chloropropyl)benzene, 1-phenylcarbonyl-4-(2-chloropropyl)benzene, 1-methoxycarbonyl-4-(2-chloropropyl)benzene, 1-phenoxycarbonyl-4-(2-chloropropyl)benzene, 1-sulfonyl-4-(2-chloropropyl)benzene, 1-trifluoromethyl-4-(2-chloropropyl)benzene, 3,5-bis-trifluoromethyl-1-(2-chloropropyl)benzene, 1,2,3,4,5-pentafluoro-6-(2-chloropropyl)benzene, 2-(2-chloropropyl)pyridine, 2-(2-bromopropyl)pyridine, 1-(2-chloropropyl)-1H-pyrrole, 1-(2-bromopropyl)-1H-pyrrole, 2-(2-chloropropyl)furan, 2-(2-bromopropyl)furan, 2-(2-chloropropyl)thiophene, 2-(2-bromopropyl)thiophene, 2-chloro-2-methyl-propionaldehyde, 2-bromo-2-methyl-propionaldehyde, 3-chloro-3-methyl-butan-2-one, 3-bromo-3-methyl-butan-2-one, 2-chloro-2-methyl-1-phenyl-propan-1-one, 2-bromo-2-methyl-1-phenyl-propan-1-one, 2-chloro-2-methyl-propionic acid, 2-bromo-2-methyl-propionic acid, methyl 2-chloro-2-methyl-propionate, methyl 2-bromo-2-methyl-propionate, ethyl 2-chloro-2-methyl-propionate, ethyl 2-bromo-2-methyl-propionate, n-propyl 2-chloro-2-methyl-propionate, n-propyl 2-bromo-2-methyl-propionate, n-butyl 2-chloro-2-methyl-propionate, n-butyl 2-bromo-2-methyl-propionate, phenyl 2-chloro-2-methyl-propionate, phenyl 2-bromo-2-methyl-propionate, 2-chloro-2-methylpropylnitrile, 2-bromo-2-methyl-propylnitrile, etc.

Examples of compounds represented by the formula (5) are as follows

Examples of groups represented by $R^3$, $R^4$ and $R^5$ are as given above.

Examples of compounds usable are those wherein halogen atom is replaced by hydrogen atom in the compound represented by the formula (4).

Next, a detailed description will be given of the process for preparing the compound (1).

(A) Process of Using the Compound (3) and the Compound (5):

The compound (5) is dissolved in a solvent. Examples of solvents usable are N,N-dimethylformamide (DMF), diakyl ether, tetrahydrofuran (THF), dimethoxyethane and like ethers, toluene, xylene and like aromatic solvents, hexane and like aliphatic hydrocarbons. THF is preferable. The amount of solvent to be used, which is suitably adjusted, is 1 to 100 ml, preferably 5 to 20 ml, per gram of the compound (5).

To the solution is slowly added dropwise lithium diisopropylamide (LDA), lithium hexamethyldisilazide, lithium 2,2,6,6-tetramethylpiperizide or like lithium amide compound, potassium diisopropylamide, potassium hexamethyldisilazide, potassium 2,2,6,6-tetramethylpiperizide, potassium amide ($KNH_2$) or like potassium amide compound, or sodium amide, followed by stirring. The reaction time differs with the reaction temperature and pressure and is usually 5 minutes to 24 hours, preferably 10 minutes to 2 hours. The reaction temperature is −150° C. to 80° C., preferably −100° C. to 80° C., more preferably −78° C. to 80° C., most preferably −78° C. to 20° C. The reaction is carried out usually under atmospheric pressure, but may be carried out at increased pressure or in a vacuum. Next, a compound (3) is added to the reaction mixture, followed by stirring. The reaction time differs with the reaction temperature and pressure and is usually 5 minutes to 24 hours, preferably 10 minutes to 2 hours. The reaction temperature is −78° C. to 80° C., preferably −78° C. to 20° C., more preferably −50° C. to 20° C. The reaction is carried out usually under atmospheric pressure, but may be carried out at increased pressure or in a vacuum.

The proportion of the compound (5) to the compound (3) is 0.5 to 1.5 moles, preferably 0.8 to 1.2 moles of the compound (5), per mole of the compound (3).

After the completion of the reaction, the solvent is concentrated, and the desired compound is isolated and purified. Although the method of purification can be determined suitably depending on the compound, usually vacuum distillation or recrystallization is preferable.

(B) Process of Using the Compound (3) and the Compound (4):

The compound (3) is dissolved in a solvent. Examples of solvents usable are liquid ammonia, mixed solvent of liquid ammonia and tetrahydrofuran, mixed solvent of liquid ammonia and ether, mixed solvent of liquid ammonia and 1,4-dioxane or the like. The amount of solvent to be used, which is suitably adjusted, is 1 to 100 ml, preferably 5 to 20 ml, per gram of the compound (3).

To the solution is slowly added dropwise metal magnesium, metal sodium, metal potassium, metal lithium, sodium bromide, ammonium bromide or the like, followed by stirring. The reaction temperature is −78° C. to 30° C., preferably −78° C. to 0° C. The reaction is carried out usually under atmospheric pressure, but may be carried out at increased pressure or in a vacuum.

Next, a compound (4) is added to the reaction mixture, followed by stirring. The reaction time differs with the reaction temperature and pressure and is usually 5 minutes to 24 hours, preferably 10 minutes to 2 hours. The reaction temperature is −78° C. to 30° C., preferably −78° C. to 0° C. The reaction is carried out usually under atmospheric pressure, but may be carried out at increased pressure or in a vacuum.

The proportion of the compound (4) to the compound (3) is 0.5 to 1.5 moles, preferably 0.8 to 1.2 moles of the compound (4), per mole of the compound (3). After the completion of the reaction, the solvent is concentrated, and the desired compound is isolated and purified. Although the method of purification can be determined suitably depending on the compound, usually vacuum distillation or recrystallization is preferable.

A living radical polymerization initiator of the present invention is represented by the formula (2)

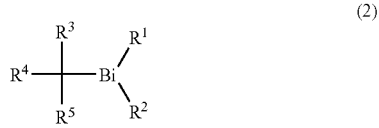

(2)

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, amido, oxycarbonyl or cyano.

Examples of groups represented by $R^1$ to $R^5$ are as given above.

An azo type polymerization initiator used in the present invention is not particularly limited insofar as it is usable in a usual radical polymerization. Example thereof are 2,2'-azobis-isobutyronitrile (AIBN), 2,2'-azobis(2-methylbutyronitrile) (AMBN), 2,2'-azobis(2,4-dimethylvaleronitrile) (ADVN), 1,1'-azobis(1-cyclohexanecarbonitrile) (ACHN), dimethyl-2,2'-azobisisobutyrate (MAIB), 4,4'-azobis(4-cyanovaleric acid) (ACVA), 1,1'-azobis(1-acetoxy-1-phenylethane), 2,2'-azobis(2-methylbutylamide), 2,2'-azobis(4-methoxy-2,4-dimethylvaleronitrile), 2,2'-azobis(2-methylamidinopropane) dihydrochloride, 2,2'-azobis[2-(2-imidazoline-2-yl)propane], 2,2'-azobis[2-methyl-N-(2-hydroxyethyl)propionamide], 2,2'-azobis(2,4,4-trimethylpentane), 2-cyano-2-propylazoformamide, 2,2'-azobis(N-butyl-2-methylpropionamide) and 2,2'-azobis(N-cyclohexyl-2-methylpropionamide).

These azo type polymerization initiators are preferably selected depending on the reaction conditions. For example, in case of low temperature polymerization, preferable are 2,2'-azobis(2,4-dimethylvaleronitrile) (ADVN) and 2,2'-azobis(4-methoxy-2,4-dimethylvaleronitrile). In case of middle temperature polymerization, preferable are 2,2'-azobisisobutyronitrile (AIBN), 2,2'-azobis(2-methylbutyronitrile) (AMBN), dimethyl-2,2'-azobisisobutyrate (MAIB) and 1,1'-azobis(1-acetoxy-1-phenylethane). In case of high temperature polymerization, preferable are 1,1'-azobis(1-cyclohexanecarbonitrile) (ACHN), 2-cyano-2-propylazoformamide, 2,2'-azobis(N-butyl-2-methylpropionamide), 2,2'-azobis(N-cyclohexyl-2-methylpropionamide) and 2,2'-azobis(2,4,4-trimethylpentane). In case of using aqueous solvent, preferable are 4,4'-azobis(4-cyanovaleric acid) (ACVA), 2,2'-azobis(2-methylbutylamide), 2,2'-azobis(2-methylamidinopropane) dihydrochloride, 2,2'-azobis[2-(2-imidazoline-2-yl)propane] and 2,2'-azobis[2-methyl-N-(2-hydroxyethyl)propionamide].

The vinyl monomer to be used in the present invention is not particularly limited insofar as the monomer can be subjected to radical polymerization. Examples of vinyl monomers usable are as follows.

Methyl(meth)acrylate, ethyl(meth)acrylate, propyl (meth)acrylate, butyl(meth)acrylate, octyl(meth)acrylate, lauryl (meth)acrylate, (meth)acrylic acid 2-hydroxyethyl ester and like (meth)acrylic acid esters, cyclohexyl (meth)acrylate, methylcyclohexyl(meth)acrylate, isobornyl (meth)acrylate, cyclododecyl(meth)acrylate and like cycloalkyl-containing unsaturated monomers.

(Meth)acrylic acid, maleic acid, fumaric acid, itaconic acid, citraconic acid, crontonic acid, maleic anhydride, methyl and like carboxyl-containing unsaturated monomers.

N,N-Dimethylaminopropyl(meth)acrylamide, N,N-dimethylaminoethyl(meth)acrylamide, 2-(dimethylamino)ethyl (meth)acrylate, N,N-dimethylaminopropyl(meth)acrylate and like unsaturated monomers containing a tertiary amine.

N-2-Hydroxy-3-acryloyloxypropyl-N,N,N-trimethylammonium chloride, N-methacryloylaminoethyl-N,N,N-dimethylbenzylammonium chloride and like unsaturated monomers containing quaternary ammonium base.

Glycidyl(meth)acrylate and like epoxy-containing unsaturated monomers.

Styrene, α-methylstyrene, 4-methylstyrene (p-methylstyrene), 2-methylstyrene (o-methylstyrene), 3-methylstyrene (m-methylstyrene), 4-methoxystyrene (p-methoxystyrene), p-t-butylstyrene, p-n-butylstyrene, p-tert-butoxystyrene, 2-hydroxymethylstyrene, 2-chlorostyrene (o-chlorostyrene), 4-chlorostyrene (p-chlorostyrene), 2,4-dichlorostyrene, 1-vinylnaphthalene, divinylbenzene, p-styrenesulfonic acid or an alkali metal salt thereof (sodium salt or potassium salt, etc.) and like aromatic unsaturated monomers (styrene type monomer).

2-Vinylthiophene, N-methyl-2-vinylpyrrole, 1-vinyl-2-pyrrolidone, 2-vinylpyridine, 4-vinylpyridine and like unsaturated monomers containing a heterocyclic ring.

N-Vinylformaldehyde, N-vinylacetamide and like vinylamides.

(Meth)acrylamide, N-methyl(meth)acrylamide, N-isopropyl-(meth)acrylamide, N,N-dimethyl(meth)acrylamide and like (meth)acrylamide type monomers.

1-Hexene, 1-octene, 1-decene and like α-olefins.

Butadiene, isoprene, 4-methyl-1,4-hexadiene, 7-methyl-1,6-octadiene and like dienes.

Vinyl acetate, vinyl benzoate and like vinyl carboxylate.

Hydroxyethyl(meth)acrylate, (meth)acrylonitrile, methyl vinyl ketone, vinyl chloride, vinylidene chloride.

Preferable among these are (meth)acrylic acid ester, unsaturated monomers containing a cycloalkyl group, aromatic unsaturated monomers (styrene type monomers), (meth)acrylamide type monomers, (meth)acrylonitrile and methyl vinyl ketone.

Examples of preferable (meth)acrylic acid ester monomers are methyl(meth)acrylate, ethyl(meth)acrylate, propyl(meth)acrylate, butyl(meth)acrylate and (meth)acrylic acid 2-hydroxyethyl ester. Especially preferable are methyl methacrylate, ethyl methacrylate, propyl methacrylate, butyl methacrylate and methacrylic acid 2-hydroxyethyl ester.

Examples of preferable unsaturated monomers containing a cycloalkyl group are cyclohexyl(meth)acrylate and isobornyl(meth)acrylate. Especially preferable are cyclohexyl methacrylate and isobornyl methacrylate.

Examples of preferable styrene type monomers are styrene, α-methylstyrene, o-methylstyrene, p-methylstyrene, p-methoxystyrene, p-t-butylstyrene, p-n-butylstyrene, p-tert-butylstyrene, p-chlorostyrene, and p-styrenesulfonic acid or an alkali metal salt thereof (sodium salt or potassium salt, etc.). More preferable are styrene and p-chlorostyrene.

Example of preferable (meth)acrylamide type monomers is N-isopropyl-(meth)acrylamide. Especially preferable is N-isopropyl-methacrylamide.

The term "(meth)acrylic acid" refers collectively to "acrylic acid" and "methacrylic acid."

Also useful are vinyl monomers of the formula (6)

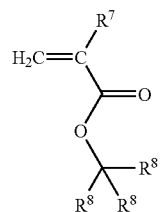

(6)

wherein $R^7$ is hydrogen, methyl, trifluoromethyl or hydroxymethyl, and the groups $R^8$ are each independently of the other a monovalent alicyclic hydrocarbon group having 4 to 20 carbon atoms or a derivative thereof, or straight-chain or branched alkyl having 1 to 4 carbon atoms, at least one of the groups $R^8$ is the alicyclic hydrocarbon group or a derivative thereof, or two of the groups $R^8$, when taken together with the carbon atom to which they are attached, form a bivalent alicyclic hydrocarbon group having 4 to 20 carbon atoms or a derivative thereof, and the remaining group or groups $R^8$ being straight-chain or branched alkyl having 1 to 4 carbon atoms or a monovalent alicyclic hydrocarbon group having 4 to 20 carbon atoms or a derivative thereof.

Examples of monovalent alicyclic hydrocarbon groups having 4 to 20 carbon atoms or derivatives thereof represented by $R^8$, examples of alicyclic hydrocarbon groups or derivatives thereof represented by at least one of the groups $R^8$, or examples of bivalent alicyclic hydrocarbon groups having 4 to 20 carbon atoms or derivatives thereof and represented by two of the groups $R^8$ as taken together with the carbon atom to which they are attached are groups comprising an alicyclic ring and derived from cycloalkanes such as bicyclo[2.2.1]heptane, tricyclo[5.2.1.0$^{2,6}$]decane, tetracyclo[6.2.1$^{3,6}$.0$^{2,7}$]dodecane, adamantane, cyclopentane and cyclohexane; and groups comprising such an alicyclic ring and substituted with at least one kind of or at least one of straight-chain, branched or cyclic alkyl groups having 1 to 4 carbon atoms, such as methyl, ethyl, n-propyl, i-propyl, n-butyl, 2-methylpropyl, 1-methylpropyl and tert-butyl.

Examples of derivatives of monovalent or bivalent alicyclic hydrocarbon groups represented by $R^8$ are groups having at least one kind of or at least one of substituents including hydroxyl; carboxyl; oxo (i.e., the group =O); hydroxyalkyl groups having 1 to 4 carbon atoms, such as hydroxymethyl, 1-hydroxyethyl, 2-hydroxyethyl, 1-hydroxypropyl, 2-hydroxypropyl, 3-hydroxypropyl, 2-hydroxybutyl, 3-hydroxybutyl and 4-hydroxybutyl; alkoxyl groups having 1 to 4 carbon atoms, such as methoxy, ethoxy, n-propoxy, i-propoxy, n-butoxy, 2-methylpropoxy, 1-methylpropoxy and tert-butoxy; cyano; and cyanoalkyl groups having 2 to 4 carbon atoms, such as cyanomethyl, 2-cyanomethyl, 3-cyanopropyl and 4-cyanobutyl. Preferable among these substituents are hydroxyl, carboxyl, hydrdoxymethyl, cyano, cyanomethyl, etc.

Examples of straight-chain or branched alkyl groups having 1 to 4 carbon atoms and represented by $R^8$ are methyl, ethyl, n-propyl, i-propyl, n-butyl, 2-methylpropyl, 1-methylpropyl, tert-butyl, etc. Preferable among these alkyl groups are methyl, ethyl, n-propyl and i-propyl.

Given below are examples of preferred functional group side chains forming —C($R^8$)$_3$ in the formula (6).

1-Methyl-1-cyclopentyl, 1-ethyl-1-cyclopentyl, 1-methyl-1-cyclohexyl, 1-ethyl-1-cyclohexyl, 2-methyladamantane-2-yl, 2-methyl-3-hydroxyadamantane-2-yl, 2-ethyladamantane-2-yl, 2-ethyl-3-hydroxyadamantane-2-yl, 2-n-propyladamantane-2-yl, 2-n-propyl-3-hydroxyadamantane-2-yl, 2-isopropyladamantane-2-yl, 2-isopropyl-3-hydroxyadamantane-2-yl, 2-methylbicyclo[2.2.1]hept-2-yl, 2-ethylbicyclo[2.2.1]hept-2-yl, 8-methyltricyclo[5.2.1.0$^{2,6}$]deca-8-yl, 8-ethyltricyclo[5.2.1.0$^{2,6}$]deca-8-yl, 4-methyl-tetracyclo[6.2.1.1$^{3,6}$.0$^{2,7}$]dodeca-4-yl, 4-ethyl-tetracyclo[6.2.1.1$^{3,6}$.0$^{2,7}$]dodeca-4-yl, 1-(bicyclo[2.2.1]hept-2-yl)-1-methylethyl, 1-(tricyclo[5.2.1.0$^{2,6}$]deca-8-yl)-1-methylethyl, 1-(tetracyclo[6.2.1.1$^{3,6}$.0$^{2,7}$]deca-4-yl)-1-methylethyl, 1-(adamantane-1-yl)-1-methylethyl, 1-(3-hydroxyadamantane-1-yl)-1-methylethyl, 1,1-dicyclohexylethyl, 1,1-di(bicyclo[2.2.1]hept-2-yl)ethyl, 1,1-di(tricyclo[5.2.1.0$^{2,6}$]deca-8-yl)ethyl, 1,1-di(tetracyclo[6.2.1.1$^{3,6}$.0$^{2,7}$]dodeca-4-yl)ethyl, 1,1-di(adamantane-1-yl)ethyl, etc.

Further, preferable examples of the vinyl monomers of the formula (6) are as follows.

(Meth)acrylic acid 1-methyl-1-cyclopentyl ester, (meth)acrylic acid 1-ethyl-1-cyclopentyl ester, (meth)acrylic acid 1-methyl-1-cyclohexyl ester, (meth)acrylic acid 1-ethyl-1-cyclohexyl ester, (meth)acrylic acid 2-methyladamantane-2-yl ester, (meth)acrylic acid 2-methyl 3-hydroxyadamantane-2-yl ester, (meth)acrylic acid 2-ethyladamantane-2-yl ester, (meth)acrylic acid 2-ethyl 3-hydroxyadamantane-2-yl ester, (meth)acrylic acid 2-n-propyl-adamantane-2-yl ester, (meth)acrylic acid 2-n-propyl 3-hydroxyadamantane-2-yl ester, (meth)acrylic acid 2-isopropyladamantane-2-yl ester, (meth)acrylic acid 2-isopropyl 3-hydroxyadamantane-2-yl ester, (meth)acrylic acid 2-methyladamantane-2-yl ester, (meth)acrylic acid 2-methylbicyclo[2.2.1]hept-2-yl ester, (meth)acrylic acid 2-ethylbicyclo[2.2.1]hept-2-yl ester, (meth)acrylic acid 8-methyltricyclo[5.2.1.0$^{2,6}$]deca-8-yl ester, (meth)acrylic acid 8-ethyltricyclo[5.2.1.0$^{2,6}$]deca-8-yl ester, (meth)acrylic acid 4-methyltetracyclo[6.2.1.1$^{2,6}$.0$^{2,7}$]-dodeca-4-yl ester, (meth)acrylic acid 4-ethyltetracyclo[6.2.1.1$^{3,6}$.0$^{2,7}$]dodeca-4-yl ester, (meth)acrylic acid 1-(bicyclo[2.2.1]hept-2-yl)-1-methyl ester, (meth)acrylic acid 1-(tricyclo[5.2.1.0$^{2,6}$]deca-8-yl)-1-methyl ester, (meth)acrylic acid 1-(tetracyclo[6.2.1.1$^{3,6}$.0$^{2,7}$]dodeca-4-yl)-1-methylethyl ester, (meth)acrylic acid 1-(adamantane-1-yl)-1-methylethyl ester, (meth)acrylic acid 1-(3-hydroxyadamantane-1-yl)-1-methylethyl ester, (meth)acrylic acid 1,1-dicyclohexylethyl ester, (meth)acrylic acid 1,1-di(bicyclo[2.2.1]hept-2-yl)ethyl ester, (meth)acrylic acid 1,1-di(tricyclo[5.2.1.0$^{2,6}$]deca-8-yl)ethyl ester, (meth)acrylic acid 1,1-di(tetracyclo[6.2.1.1$^{3,6}$.0$^{2,7}$]dodeca-4-yl)ethyl ester and (meth)acrylic acid 1,1-di(adamantane-1-yl)ethyl ester.

Especially preferable examples of the vinyl monomers of the formula (6) are (meth)acrylic acid 1-methyl-1-cyclopentyl ester, (meth)acrylic acid 1-ethyl-1-cyclopentyl ester, (meth)acrylic acid 1-methyl-1-cyclohexyl ester, (meth)acrylic acid 1-ethyl-1-cyclohexyl ester, (meth)acrylic acid 2-methyladamantane-2-yl ester, (meth)acrylic acid 2-ethyladamantane-2-yl ester, (meth)acrylic acid 2-n-propyladamantane-2-yl ester, (meth)acrylic acid 2-isopropyladamantane-2-yl ester and (meth)acrylic acid 1-(adamantane-1-yl)-1-methylethyl ester.

Specifically stated, the living radical polymer of the present invention is produced by the process to be described below.

A vinyl monomer, a living radical polymerization initiator of the formula (2), and as required an azo type polymerization initiator are mixed together in a container having its inside air replaced by an inert gas. Next, the mixture is then stirred. The reaction temperature and the reaction time may be adjusted suitably. The mixture is stirred usually at 20 to 150° C. for 1 minute to 100 hours, preferably at 40 to 100° C. for 0.1 to 30 hours. The reaction is carried out usually under atmospheric pressure, but may be carried out at increased pressure or in a vacuum. Examples of inert gases usable at this time are nitrogen, argon, helium, etc., among which argon and nitrogen are preferred. Nitrogen is especially preferred.

Although the vinyl monomer and the living radical polymerization initiator of the formula (2) are used in amounts which are suitably adjusted depending on the molecular weight and molecular weight distribution of the living radical polymer to be obtained, usually 5 to 10,000 moles, preferably 50 to 5,000 moles, of the vinyl monomer is used per mole of the living radical polymerization initiator of the formula (2).

In case of combined use of the living radical polymerization initiator of the formula (2) and the azo type polymerization initiator, the latter is used in the ratio of usually 0.01 to 100 moles, preferably 0.1 to 10 moles, especially preferably 0.1 to 5 moles, per mole of the former. The vinyl monomer is used in an amount of 5 to 10,000 moles, preferably 50 to 5,000 moles, per mole of the living radical polymerization initiator of the formula (2).

The polymerization reaction is carried out usually in the absence of solvent, while an organic solvent generally in use for radical polymerization or an aqueous solvent may be used. Examples of organic solvents usable are benzene, toluene, N,N-dimethylformamide (DMF), dimethyl sulfoxide (DMSO), acetone, 2-butanone (methyl ethyl ketone), dioxane, hexafluoroisopropanol, chloroform, carbon tetrachloride, tetrahydrofuran (THF), ethyl acetate, trifluoromethylbenzene, etc. Examples of aqueous solvents are water, methanol, ethanol, isopropanol, n-butanol, ethyl cellosolve, butyl cellosolve, 1-methoxy-2-propanol, diacetonealcohol, etc. The amount of the solvent to be used is adjusted suitably. For example, 0.01 to 50 ml, preferably 0.05 to 10 ml, more preferably 0.1 to 1 ml, of the solvent is used per gram of the vinyl monomer.

Next, the mixture is then stirred. The reaction temperature and the reaction time may be adjusted suitably in accordance with the molecular weight or molecular weight distribution of the living radical polymer to be obtained. The mixture is stirred usually at 20 to 150° C. for 1 minute to 100 hours, preferably at 40 to 100° C. for 0.1 to 30 hours. The mixture is stirred more preferably at 40 to 80° C. for 0.1 to 15 hours. Thus, the present invention has a feature that a high yield and precise PD are performed even at such a low polymerization temperature and short period of polymerization time. The reaction is carried out usually under atmospheric pressure, but may be carried out at increased pressure or in a vacuum.

After the completion of the reaction, the solvent used and the remaining monomer are removed in a vacuum to take out the desired polymer, or the desired polymer is isolated by re-precipitation using a solvent wherein the polymer is insoluble. The reaction mixture can be treated by any method insofar as it causes no problem to the desired polymer.

According to the invention, it is possible to use the emulsion polymerization process wherein a surfactant is used to carry out polymerization mainly in a micelle. When required, a dispersant of water-soluble high polymer, such as a polyvinyl alcohol, may be used. Such surfactants are usable singly, or at least two of them can be used in combination. The surfactant is used preferably in an amount of 0.3 to 50 parts by weight, more preferably 0.5 to 50 parts by weight, per 100 parts by weight of all monomers. Water is used preferably in an amount of 50 to 2000 parts by weight, more preferably 70 to 1500 parts by weight, per 100 parts by weight of all monomers. The polymerization temperature is preferably in the range of 0 to 100° C., more preferably 40 to 90° C., although not limited particularly. The reaction time is suitably determined so as to complete the polymerization reaction, for example, in accordance with the reaction temperature, or with the monomer composition to be used and the kind of surfactant and polymerization initiator. The reaction time is preferably within 24 hours.

According to the invention, the suspension polymerization process is also usable in which a dispersant is used to conduct polymerization generally without using any micelle. Also usable along with the dispersant are auxiliary dispersants such as sodium chloride, potassium chloride, sodium sulfate, potassium sulfate and manganese sulfate when so required. Such stabilizers for dispersion in water are used preferably in an amount of 0.01 to 30 parts by weight, more preferably 0.05 to 10 parts by weight, and most preferably 0.1 to 5 parts by weight, per 100 parts by weight of the monomers. Water is used preferably in an amount of 50 to 2000 parts by weight, more preferably 70 to 1500 parts by weight, per 100 parts by weight of the monomers. The polymerization temperature is preferably in the range of 0 to 100° C., more preferably 40 to 90° C., although not limited particularly. The reaction time is suitably determined so as to complete the polymerization reaction, for example, in accordance with the reaction temperature, or with the monomer composition to be used and the kind of water dispersion stabilizer and polymerization initiator. The reaction time is preferably within 24 hours.

The miniemulsion polymerization process is further usable according to the invention. The monomer is forcibly dispersed using a surfactant and cosurfactant and also using a homogenizer or ultrasonic device, but generally without using any micelle. Such surfactant and cosurfactant are used in an amount of 0.3 to 50 parts by weight, preferably 0.5 to 50 parts, based on all the monomers. The ultrasonic irradiation time is 0.1 to 10 minutes, preferably 0.2 to 5 minutes.

According to the present invention, at least one compound selected from among a ditelluride compound, distibine compound and dibismuthine compound can be admixed with the living radical polymerization initiator of the formula (2), or with a mixture of this initiator and an azo polymerization initiator as required, for the polymerization of the vinyl monomer. Stated more specifically, the present invention provides, for example, a process for preparing a living radical polymer by polymerizing the vinyl monomer using a mixture of the living radical polymerization initiator of the formula (2) and at least one compound selected from among a ditelluride compound, distibine compound and dibismuthine compound, and a process for preparing a living radical polymer by polymerizing the vinyl monomer using a mixture of the living radical polymerization initiator of the formula (2), an azo polymerization initiator and at least one compound selected from among a ditelluride compound, distibine compound and dibismuthine compound.

The ditelluride compound to be used in the present invention can be a known ditelluride compound or one prepared by a common process. Examples of preparation processes are those disclosed in WO 2004-014962 and WO2004-096870.

Examples of ditelluride compounds are dimethyl ditelluride, diethyl ditelluride, di-n-propyl ditelluride, diisopropyl ditelluride, dicyclopropyl ditelluride, di-n-butyl ditelluride, di-sec-butyl ditelluride, di-tert-butyl ditelluride, dicyclobutyl ditelluride, diphenyl ditelluride, bis(p-methoxyphenyl)ditelluride, bis(p-aminophenyl)ditelluride, bis(p-nitrophenyl)ditelluride, bis(p-cyanophenyl)ditelluride, bis(p-sulfonylphenyl)ditelluride, dinaphthyl ditelluride, dipyridyl ditelluride, etc.

The distibine compound to be used in the present invention can be a known distibine compound or one prepared by a common process. Examples of preparation processes are those disclosed in J. Organomet. Chem., 1973, Vol. 51, p. 223; Organometallics, 1982, Vol. 1, p. 1408; and Organometallics, 1983, Vol. 2, p. 1859.

Examples of distibine compounds are tetramethyldistibine, tetraethyldistibine, tetraisopropyldistibine, tetrabutyldistibine, tetravinyldistibine, tetraisopropenyldistibine, tetraisobutenyldistibine, tetraphenyldistibine, tetrakis(trimethylsilyl)distibine, 1,1'-bistibolane, tetramethyldistiboryl, etc.

The dibismuthine compound to be used in the present invention can be a known dibismuthine compound or one prepared by a common process. Examples of preparation processes are those disclosed in Chem. Z., 1977, Vol. 101, p. 399; and J. Organomet. Chem., 1980, Vol. 186, p. C5.

Examples of dibismuthine compounds are tetramethyldibismuthine, tetraethyldibismuthine, tetrapropyldibismuthine, tetraisopropyldibismuthine, tetrabutyldibismuthine, tetraisopropenyldibismuthine, tetraisobutenyldibismuthine, tetraphenyldibismuthine, tetrakis(trimethylsilyl)dibismuthine, 1,1,2,2-tetrakis(bis(trimethylsilyl)methyl)dibismuthine, 1,1'-bibismolane, etc.

In the case where a living radical polymer is prepared by admixing at least one compound selected from among a ditelluride compound, distibine compound and dibismuthine compound with a living radical polymerization initiator of the formula (2), or with a mixture of this initiator and an azo polymerization initiator as required, and polymerizing a vinyl monomer with use of the resulting mixture, this process can be practiced in the same manner the above-mentioned living radical polymer preparing process. Stated more specifically, the process is the same as the foregoing living radical polymer preparing process with the exception of admixing at least one compound selected from among a ditelluride compound, distibine compound and dibismuthine compound with a living radical polymerization initiator of the formula (2), or with a mixture of this initiator and an azo polymerization initiator as required, in a vessel in which the inside air is replaced with an inert gas.

The living radical polymerization initiator of the formula (2) and at least one compound selected from among a ditelluride compound, distibine compound and dibismuthine compound are used usually in such amounts that the compound selected from among a ditelluride compound, distibine compound and dibismuthine compound is used in an amount of 0.1 to 100 moles, preferably 0.1 to 10 moles, more preferably 0.1 to 5 moles, per mole of the living radical polymerization initiator of the formula (2).

The living radical polymerization initiator of the present invention is adapted for excellent control of molecular weights and molecular weight distributions under very mild conditions. In particular, in case of combined use of the present living radical polymerization initiator and the azo type polymerization initiator, the present polymerization reaction proceeds in a shortened reaction time than the conventional living radical polymerization reaction.

Different kinds of vinyl monomers are usable in the process of the invention for preparing a living radical polymer. For example when at least two kinds of vinyl monomers are reacted at the same time, a random copolymer can be obtained. The random copolymer obtained is a polymer which comprises the reacted monomers in the original ratio (mole ratio) regardless of the kinds of the monomers. When a random copolymer is obtained by reacting a vinyl monomer A and a vinyl monomer B at the same time, the copolymer has substantially the same material ratio (mole ratio). Further when two kinds of vinyl monomers are reacted in succession, a block copolymer can be obtained. The block copolymer is provided by the same order of reacted monomers regardless of the kinds of the monomers. When a vinyl monomer A and a vinyl monomer B are reacted to obtain a block copolymer, the polymer obtained is in the order of A-B or B-A in conformity with the order of monomers reacted.

The living radical polymer to be obtained by the invention is adjustable in molecular weight according to the reaction time and the amount of the organobismuth compound, and can be 500 to 1,000,000 in number average molecular weight. The invention is especially suitable for producing living radical polymers having a number average molecular weight of 1,000 to 50,000.

The living radical polymer to be obtained by the invention is controlled to 1.04 to 1.50 in molecular weight distribution (PD=Mw/Mn). The molecular weight distribution is controllable to a narrower range of 1.05 to 1.50, a further narrower range of 1.05 to 1.30, a still narrower range of 1.10 to 1.20, 1.09 to 1.20, 1.09 to 1.17, 1.09 to 1.12. Among these, most preferable is 1.04 to 1.12.

It has been found that the living radical polymer of the present invention has a growth terminal which is highly reactive organobismuthanyl group. Accordingly, the organobismuth compound used for radical polymerization makes it easier to convert the terminal group to other functional group than in the case of the living radical polymer obtained by conventional living radical polymerization.

The living radical polymer obtained according to the invention is therefore usable as a macro living radical polymerization initiator (macroinitiator).

A-B diblock copolymers such as methyl methacrylate-styrene and B-A diblock copolymers such as styrene-methyl methacrylate can be obtained using a macro living radical polymerization initiator of the invention. A-B-A triblock copolymers such as methyl methacrylate-styrene-methyl methacrylate and A-B-C triblock copolymers such as methyl methacrylate-styrene-butyl acrylate are also available. This is attributable to the fact that the vinyl monomers of various different types are controllable by the living radical polymerization initiator of the formula (2), and as required the azo type polymerization initiator, and also to the fact that highly reactive bismuthanyl group is present at the growth terminal of the living radical polymer obtained with use of the living radical polymerization initiator.

Stated more specifically, block copolymers are prepared by the processes to be described below.

For preparing A-B diblock copolymers such as methyl methacrylate-styrene copolymer, methyl methacrylate, the living radical polymerization initiator of the formula (2), and as required the azo type polymerization initiator and a ditelluride compound etc. are mixed together first as in the process described above for preparing a living radical polymer to obtain poly(methyl methacrylate), and subsequently mixing styrene with the polymer to obtain methyl methacrylate-styrene copolymer.

A-B-A triblock copolymers and A-B-C triblock copolymers can be produced, for example, by preparing an A-B diblock copolymer by the above process and thereafter mixing a vinyl monomer (A) or vinyl monomer (C) with the copolymer to obtain the A-B-A or A-B-C triblock copolymer.

In producing the diblock copolymer according to the invention, the living radical polymerization initiator of the formula (2), and as required the azo type polymerization initiator and a ditelluride compound, etc. can be used when a homopolymer is prepared from the first monomer and/or when the diblock copolymer is subsequently prepared.

Further in producing the triblock copolymer according to the invention, the living radical polymerization initiator of the formula (2), and as required the azo type polymerization initiator and a ditelluride compound, etc. can be used at least once when a homopolymer is prepared from the first monomer, or when a diblock copolymer is subsequently prepared, or when the triblock copolymer is subsequently prepared.

The preparation of each block may be followed directly by the subsequent reaction for the next block, or the subsequent reaction for the next block may be initiated after the purification of the product resulting from the completion of the first reaction. The block copolymer can be isolated by a usual method. For example, the solvent used and the remaining monomer are removed in a vacuum to take out the desired polymer, or the desired polymer is isolated by re-precipitation using a solvent wherein the polymer is insoluble.

A resin containing an acid-dissociable group can be prepared by polymerizing a vinyl monomer using the living radical polymerization initiator of the invention and removing the growth terminal of the resulting living radical polymer. This resin is precision-controlled in molecular weight and molecular weight distribution (PD=Mw/Mn), is highly soluble in resist solvents and can be used suitably for resists for use in manufacturing semiconductor devices which are expected to be finer in structure.

In the case where the living radical polymerization initiator of the formula (2) is used, a metal atom remains at the growth terminal. It is desired that the amount of the remaining metal atom be up to 25 ppm based on the whole amount of the resin to ensure improvements in resist characteristics including the sensitivity and resolution of the resist and process stability.

After the polymer has been formed, the metal atom remaining at the terminal of the molecule is removed by a radical reduction method using tributylstannane or a thiol compound, an adsorption method using activated carbon, silica gel, activated alumina, activated clay, molecular sieves or high polymer adsorbent, a metal adsorption method using an ion exchange resin, a liquid-liquid extraction method for removing remaining metal compounds by the combination of water for washing and a suitable solvent, a solution purification method using ultrafiltration for extracting and removing substances having a molecular weight not greater than a specified value, or a combination of such methods.

Given below are examples of methods of purifying the resin of the invention containing an acid-dissociable group. Metals and like impurities are removed by adsorbing the metal from a resin solution using a zeta potential filter, or by washing a resin solution with an aqueous acid solution of oxalic acid or sulfonic acid to remove the metal as cherated. The remaining monomer or oligomer component is removed to a value not greater than a specified level by a liquid-liquid extraction method for removing the remaining monomer or oligomer component by the combination of water for washing and a suitable solvent, a solution purification method using ultrafiltration for extracting and removing substances having a molecular weight not greater than a specified value, a reprecipitation method for removing the remaining monomer or the like by dropwise adding a resin solution to a poor solvent to solidify the resin, and a solid purification method wherein a resin slurry filtered off is washed with a poor solvent. Such methods can be used in combination.

The poor solvent to be used in the reprecipitation method is dependent, for example, on the physical properties of the resin to be purified and can not be generally exemplified. A suitable poor solvent is to be selected for use.

A radiation-sensitive resin composition can be obtained by using a radiation-sensitive acid producing agent, serving as a component for producing an acid when irradiated with radiation, in combination with the resin containing an acid-dissociable group.

The presence of the resin containing an acid-dissociable group in the radiation-sensitive resin composition renders the composition highly soluble in resist solvents, gives excellent basic properties to the resist and renders the composition extremely suitable for use in fabricating semiconductor devices which are expected to be made finer in structure.

Preferable examples of radiation-sensitive acid producing agents are triphenylsulfonium trifluoromethane-sulfonate, triphenylsulfonium nonafluoro-n-butanesulfonate, triphenylsulfonium perfluoro-n-octanesulfonate, triphenylsulfonium-2-bicyclo[2.2.1]hept-2-yl-1,1,2,2-tetrafluoroethane-sulfonate, triphenylsulfonium-2-(3-tetracyclo[4.4.0.1$^{2,5}$.1.$^{7,10}$]dodecanyl)-1,1-difluoroethane-sulfonate, triphenylsulfonium N,N-bis(nonafluoro-n-butanesulfonyl)imidate, triphenylsulfonium camphorsulfonate, 4-cyclohexylphenyldiphenylsulfonium trifluoromethanesulfonate, 4-cyclohexylphenyldiphenyl-sulfonium nonafluoro-n-butanesulfonate, 4-cyclohexylphenyldiphenylsulfonium perfluoro-n-octanesulfonate, 4-cyclohexylphenyldiphenyl-sulfonium-2-bicyclo[2.2.1]hept-2-yl-1,1,2,2-tetrafluoro-ethanesulfonate, 4-cyclohexylphenyldiphenylsulfonium-2-(3-tetracyclo[4.4.0.1$^{2,5}$.1.$^{7,10}$]dodecanyl)-1,1-difluoroethane-sulfonate, 4-cyclohexylphenyldiphenylsulfonium N,N-bis(nonafluoro-n-butanesulfonyl)imidate, 4-cyclohexylphenyl-diphenylsulfonium camphorsulfonate, 4-t-butylphenyldiphenyl-sulfonium trifluoromethanesulfonate, 4-t-butylphenyldiphenyl-sulfonium nonafluoro-n-butanesulfonate, 4-t-butylphenyl-diphenylsulfonium perfluoro-n-octanesulfonate, 4-t-butylphenyldiphenylsulfonium-2-bicyclo[2.2.1]hept-2-yl-1,1,2,2-tetrafluoroethanesulfonate, 4-t-butylphenyl-diphenylsulfonium-2-(3-tetracyclo[4.4.0.1$^{2,5}$.1$^{7,10}$]dodecanyl)-1,1-difluoroethanesulfonate, 4-t-butylphenyldiphenyl-sulfonium-N,N-bis(nonafluoro-n-butanesulfonyl)imidate, 4-t-butylphenyldiphenylsulfonium camphorsulfonate, tri(4-t-butylphenyl)sulfonium trifluoromethanesulfonate, tri(4-t-butylphenyl)sulfonium nonafluoro-n-butanesulfonate, tri(4-t-butylphenyl)sulfonium perfluoro-n-octanesulfonate, tri(4-t-butylphenyl)sulfonium-2-bicyclo[2.2.1]hept-2-yl-1,1,2,2-tetrafluoroethane-sulfonate, tri(4-t-butylphenyl)sulfonium 2-(3-tetracyclo[4.4.0.1$^{2,5}$.1$^{7,10}$]dodecanyl)-1,1-difluoroethane-sulfonate, tri(4-t-butylphenyl)sulfonium N,N-bis(nonafluoro-n-butanesulfonyl)imidate, tri(4-t-butylphenyl)sulfonium camphorsulfonate, diphenyliodonium trifluoromethane-sulfonate, diphenyliodonium nonafluoro-n-butanesulfonate, diphenyl-iodonium perfluoro-n-octanesulfonate, diphenyli-odonium-2-bicylco[2.2.1]hept-2-yl-1,1,2,2-tetrafluoroethanesulfonate, diphenyliodonium-2-(3-tetracyclo[4.4.0.1$^{2,5}$.1$^{7,10}$]dodecanyl)-1,1-difluoroethanesulfonate, diphenyliodonium N,N-bis(nonafluoro-n-butanesulfonyl)imidate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium-2-bicyclo[2.2.1]hept-2-yl-1,1,2,2-tetrafluoroethanesulfonate, bis(4-t-butylphenyl)iodonium-2-(3-tetracyclo-[4.4.0.1$^{2,5}$.1$^{7,10}$]dodecanyl)-1,1-difluoroethanesulfonate, bis(4-t-butylphenyl)iodonium-N,N-bis(nonafluoro-n-butane-sulfonyl)imidate, bis(4-t-butylphenyl)iodonium camphorsulfonate, 1-(4-n-butoxynaphthalene-1-yl)tetrahydro-thiophenium trifluoromethanesulfonate, 1-(4-n-butoxy-naphthalene-1-yl)tetrahydrothiophenium nonafluoro-n-butanesulfonate, 1-(4-n-butoxynaphthalene-1-yl)tetrahydro-thiophenium perfluoro-n-octanesulfonate, 1-(4-n-butoxynaphthalene-1-yl)tetrahydrothiophenium-2-bicyclo[2.2.1]hept-2-yl-1,1,2,2-tetrafluoroethanesulfonate, 1-(4-n-butoxynaphthalene-1-yl)tetrahydrothiophenium 2-(3-tetraccyclo[4.4.0.1$^{2,5}$.1$^{7,10}$]dodecanyl)-1,1-difluoroethane-sulfonate, 1-(4-n-butoxynaphthalene-1-yl)tetrahydro-thiophenium-N,N-bis(nonafluoro-n-butanesulfonyl)imidate, 1-(4-n-butoxynaphthalene-1-yl)tetrahydrothiophenium champhersulfonate, 1-(3,5-dimethyl-4-hydroxyphenyl)-tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)-tetrahydrothiophenium perfluoro-n-octanesulfonate, 1-(3,5-dimethyl-4-hydroxyphenyl)tetrahydrothiophenium-2-bicyclo[2.2.1]hept-2-yl-1,1,2,2-tetrafluoroethanesulfonate, 1-(3,5-dimethyl-4-hydroxyphenyl)tetrahydrothiophenium-2-(3-tetracyclo[4.4.0.1$^{2,5}$.1$^{7,10}$]dodecanyl)-1,1-difluoroethane-sulfonate, 1-(3,5-dimethyl-4-hydroxyphenyl)tetrahydro-thiophenium-N,N-bis(nonafluoro-n-butanesulfonyl)imidate, 1-(3,5-dimethyl-4-hydroxyphenyl)tetrahydrothiophenium camphorsulfonate, N-(trifluoromethanesulfonyloxy)succinimide, N-(nonafluoro-n-butanesulfonyloxy)succinimide, N-(perfluoro-n-octanesulfonyloxy)succinimide, N-(2-bicyclo[2.2.1]hept-2-yl-1,1,2,2-tetrafluoroethanesulfonyloxy)succinimide, N-(2-(3-tetracyclo[4.4.0.1$^{2,5}$.1$^{7,10}$]dodecanyl)-1,1-difluoroethane-sulfonyloxy)succinimide, N-(camphorsulfonyloxy)succinimide, N-(trifluoromethanesulfonyloxy)bicyclo[2.2.1]hept-5-en-2,3-dicarboxyimide, N-(nonafluoro-n-butanesulfonyloxy)-bicyclo[2.2.1]hept-5-en-2,3-dicarboxyimide, N-(perfluoro-n-octanesulfonyloxy)bicyclo[2.2.1]hept-5-en-2,3-dicarboxyimide, N-(2-bicyclo[2.2.1]hept-2-yl-1,1,2,2-tetrafluoroethane-sulfonyloxy)bicyclo[2.2.1]hept-5-en-2,3-dicarboxyimide, N-(2-(3-tetracyclo[4.4.0.1$^{2,5}$.1$^{7,10}$]dodecanyl)-1,1-difluoroethane-sulfonyloxy)bicyclo[2.2.1]hept-5-en-2,3-dicarboxyimide, N-(camphorsulfonyloxy)bicyclo[2.2.1]hept-5-en-2,3-dicarboxyimide, etc.

According to the invention, radiation-sensitive acid producing agents can be used singly, or at least two of them are usable in admixture.

To ensure the sensitivity of the resist and the amenability thereof to development, the radiation-sensitive acid producing agent is used usually in an amount of 0.1 to 20 parts by weight, preferably 0.1 to 7 parts by weight, per 100 parts by weight of the resin containing an acid-dissociable group. If the amount of acid producing agent is less than 0.1 part by weight, lower sensitivity and impaired developability tend to result, whereas if the amount is in excess of 20 parts by weight, lower transparency to radiation will result, making is less likely to obtain rectangular resist patterns.

BEST MODE OF CARRYING OUT THE INVENTION

The present invention will be described below in detail with reference to Examples, but is not limited thereto in any way. In Examples and Comparative Examples, properties were determined by the following methods.

Identification of organobismuth compounds and living radical polymers

The organobismuth compound was identified based on the results of $^1$H-NMR, $^{13}$C-NMR and MS analyses. The molecular weight and molecular weight distribution of the living radical polymer were determined using GPC (gel permeation chromatography). The measuring instruments used are as follows.

$^1$H-NMR: Varian VXR-300S (300 MHz)

$^{13}$C-NMR: Varian VXR-300S (300 MHz)

MS(GCMS): Hewlett Packard 5972

Molecular weight and molecular weight distribution

Apparatus: Gel permeation chromatography Japan Waters GPCV 2000

Column: TSK gel GMHXL; TSK gel G3000HXL

The following compounds were used.

Di compound (Di Compound)

Dimethylditelluride (Preparation Example 4)

Tetramethyldistibine (Preparation Example 7)

Azo type polymerization initiator:

2,2'-azobis-isobutyronitrile (Otsuka Chemical Co., Ltd., AIBN), 1,1'-azobis(1-cyclohexanecarbonitrile) (Otsuka Chemical Co., Ltd., ACHN), 2,2'-azobis-2,4-dimethylvaleronitrile (Otsuka Chemical Co., Ltd., ADVN)

Monomer:

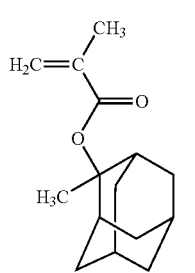 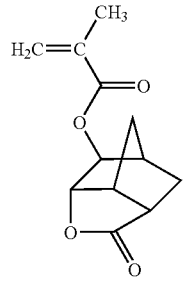

Adamantane monomer MADM     Norbornene monomer NBLM

Preparation Example 1

Preparation of Trimethylbismuthane

A solution of 25 g of bismuth tribromide in 40 ml of THF was added dropwise to 180 ml of 1.0 M methyllithium-diethyl ether solution under argon atmosphere maintaining reflux state. Thereafter, the reaction mixture was stirred at room temperature for 1.5 hours. The solvent was removed at atmospheric distillation, and then distilled in a vacuum. The distillate was again distilled, giving 8.1 g of a colorless oily product (54.8% in yield).

$^1$H-NMR revealed that the product was the desired one.
$^1$H-NMR (300 MHz, CDCl$_3$) 1.13 (s, 9H)

Preparation Example 2

Preparation of Dimethylbismuthanyl Bromide

A solution of 7.2 g of bismuth tribromide in 13 ml of THF was added dropwise to 8.0 g (31.5 mmol) of trimethylbismuthane prepared in Preparation Example 1 under argon atmosphere. Thereafter, the reaction mixture was stirred at room temperature for 1.5 hours. After the reaction mixture was filtrated with 0.2 μm membrane filter, THF was removed in a vacuum, giving 14.23 g of a light yellow amorphous product (94.5% in yield).

$^1$H-NMR revealed that the product was the desired one.
$^1$H-NMR (300 MHz, DMSO) 1.52 (s, 6H)

Preparation Example 3

Preparation of Diphenylbismuthanyl Bromide

In 400 ml of THF was dissolved 22.014 g (50 mmol) of triphenylbismuthine (Tokyo Kasei Co., Ltd.) under nitrogen atmosphere. The solution was cooled to 0° C. and thereto was slowly added dropwise 11.231 g (25 mmol) of tribromobismuthine (Aldrich Corp.) (30 minutes). The mixture was stirred to room temperature for 1 hour. The yellow precipitate was filtered and dried in a vacuum. The obtained precipitate was recrystallized from benzene, giving 27.422 g (62 mmol: yield 83%) of yellow powdery product.

$^1$H-NMR revealed that the product was the desired one.
$^1$H-NMR (400 MHz) 7.12 (tt, J=1.2 Hz, J=7.4 Hz, Aromatic proton), 7.33 (tt, J=1.2 Hz, J=7.6 Hz, 4H, Aromatic proton), 8.02 (ddd, J=0.8 Hz, J=1.6 Hz, J=6.4 Hz, 4H, Aromatic proton)

Preparation Example 4

Preparation of Dimethyl Ditelluride

A 3.19 g quantity (25 mmole) of metallic tellurium [product of Aldrich, brand name: Tellurium (−40 mesh)] was suspended in 25 ml of THF, and 25 ml (28.5 mmole) of methyllithium [product of Kanto Chemical Co, Ltd., diethyl ether solution] was added slowly to the suspension at 0° C. (10 minutes). The reaction mixture was stirred until the metallic tellurium disappeared completely (10 minutes). To the resulting reaction mixture was added 20 ml of a solution of ammonium chloride at room temperature, followed by stirring for 1 hour. The organic layer was separated off, and the aqueous layer was subjected to extraction with diethyl ether 3 times. The organic layers were collected, dried over anhydrous sodium sulfate and concentrated in a vacuum, affording 2.69 g (9.4 mmole, yield 75%) of blackish purple oil.

The product was found to be dimethyl ditelluride by MS (HRMS) and $^1$H-NMR.

HRMS (EI) m/z: Calcd for C$_2$H$_6$Te$_2$(M)$^+$, 289.8594; Found 289.8593
$^1$H-NMR (300 MHz, CDCl$_3$) 2.67 (s, 6H)

Preparation Example 5

Preparation of Trimethylstibanyl Dibromide

A methylmagnesium iodide solution was prepared by placing 37.7 g (1.55 moles) of magnesium and 235.4 g (1.65 moles) of methyl iodide into 900 ml of diethyl ether. A solution of 114 g (0.5 mole) of bismuth trichloride in 100 ml of THF was slowly added dropwise to the iodide solution at 0° C. (over a period of 40 minutes). The mixture was thereafter stirred at room temperature for 1.5 hours. A salt formed as a by-product was filtered off, and the solvent was concentrated and distilled in a vacuum (20-30° C., 200-300 mmHg). Bromine was added to the resulting liquid with stirring (until the liquid became colored owing to the addition of bromine). The precipitate obtained was washed several times with cold ether and then dried in a vacuum at room temperature, affording 115.6 g of a white solid (71% in yield). $^1$H-NMR and $^{13}$C-NMR revealed that the product was the desired one.

IR(KBr) 3007, 1792, 1720, 1394, 874, 669, 569
$^1$H-NMR (400 MHz, CDCl$_3$) 2.64 (s, 9H)
$^{13}$C-NMR (100 MHz, CDCl$_3$); 26.57

Preparation Example 6

Preparation of Dimethylstibanyl Bromide

Trimethylstibanyl dibromide prepared in Preparation Example 5 (16.3 g, 50 mmole) was heated at 180° C. in a vacuum (50 mmHg), and thereafter distilled, giving 9.27 g of dimethylstibanyl bromide (90.0% in yield) of yellow oily product.

IR(neat) 2995, 2912, 1400, 1202, 1020, 843, 768, 517
$^1$H-NMR (400 MHz, CDCl$_3$) 1.58 (s, 6H)
$^{13}$C-NMR (100 MHz, CDCl$_3$) 8.61
HRMS (EI)m/z: Calcd for C$_2$H$_6$BrSb(M)$^+$, 229.8691; Found 229.8663.

Preparation Example 7

Preparation of Tetramethyldistibine

A 465 mg quantity (19.4 mmole) of magnesium was suspended in 25 ml of THF, and a THF solution of 4.42 g (19.0 mmole) of the dimethylstibanyl bromide prepared in Preparation Example 6 was slowly added to the suspension at room temperature. The reaction mixture was thereafter stirred at 70° C. for 1 hour, the solvent was concentrated in a vacuum, 20 ml of hexane was added to an oily product obtained, and the resulting solution was collected. The collected solution was concentrated in a vacuum and subsequently distilled in a vacuum (room temperature, 0.1 mmHg) to obtain 0.30 g of an oily product (1.9 mmole, 10% in yield). $^1$H-NMR indicated that the product was tetramethyldistibine.

$^1$H-NMR (400 MHz, CDCl$_3$) 0.98 (s)

Example 1

Preparation of methyl 2-dimethylbismuthanyl-2-methylpropionate

A 2.86 g quantity (28 mmole) of methyl isobutyrate was dissolved in 25 ml of THF, and the mixture was chilled to −78° C. under argon atmosphere. To the mixture was slowly added dropwise 14.0 ml (28 mmole) of lithium diisopropylamide (Aldrich Corp., 2.0M heptane.THF.ethylbenzene solution) over a period of 10 minutes. The reaction mixture was gradually heated (one hour) and thereto was added dropwise a solution of 8.9 g of dimethylbismuthanyl bromide prepared in Preparation Example 2 in 25 ml of THF between −40° C. and −30° C. The reaction mixture was further stirred until reached to 0° C. (one hour). After the solids were filtrated with quartz wool and THF was removed in a vacuum, the reaction mixture was distilled in a vacuum, giving 4.45 g (yield 46.7%) of a yellow oily product. b.p. 59° C./2.0 mmHg.

MS (GCMS), $^1$H-NMR and $^{13}$C-NMR revealed that the product was the desired one.

$^1$H-NMR (300 MHz, CDCl$_3$) 1.08 (s, 6H, BiMe$_2$), 1.78 (s, 6H, CMe$_2$), 3.72 (s, 3H, COOMe)

$^{13}$C-NMR (300 MHz, CDCl$_3$) 10.12 (BiMe$_2$), 24.13 (Me×2), 33.11 (Bi—C, quaternaly carbon), 50.72 (OMe), 178.34 (C=O)

GCMS (EI$^+$)m/z: Calcd for C$_7$H$_{15}$O$_2$Bi(M)$^+$, 340; Found 340

Example 2

Preparation of 2-methyl-2-(dimethylbismuthanyl)-propionitrile

A 2.42 g quantity (35 mmole) of isobutyronitrile was dissolved in 20 ml of THF, and the mixture was chilled to −78° C. under argon atmosphere. To the mixture was slowly added dropwise 18 ml (36 mmole) of lithium diisopropylamide (same as above) over a period of 35 minutes. The reaction mixture was gradually heated (35 minutes) and thereto was added dropwise a solution of 11.2 g of dimethylbismuthanyl bromide prepared in Preparation Example 2 in 10 ml of THF between −40° C. and −30° C. (25 minutes). The reaction mixture was further stirred until reached to −10° C. (2 hours). After the solids were filtrated with celite and THF was removed in a vacuum, the reaction mixture was extracted with toluene. The extract was again concentrated and thereafter distilled in a vacuum, giving 0.49 g (yield 4.6%) of a white solid product. b.p. 66° C./2.5 mmHg.

$^1$H-NMR and $^{13}$C-NMR revealed that the product was the desired one.

$^1$H-NMR (300 MHz, CDCl$_3$) 1.29 (s, 6H, BiMe$_2$), 1.79 (s, 6H, CMe$_2$)

$^{13}$C-NMR (300 MHz, CDCl$_3$) 11.66 (BiMe$_2$), 19.95 (Bi—C, quaternaly carbon), 25.92 (Me×2), 128.38 (C≡N)

Example 3

Preparation of 2-methyl-2-(diphenylbismuthanyl)-propionitrile

A 0.70 ml (0.5 mmole) of diisopropylamine (Wako Pure Chemical Ind. Ltd.) was dissolved in 3 ml of THF, and the mixture was chilled to −78° C. under nitrogen atmosphere. To the mixture was slowly added dropwise 3.23 ml (5 mmole) of n-butyl lithium (Aldrich Corp., 1.6 M hexane solution). The reaction mixture was stirred at −78° C. for 10 minutes and then heated to 0° C. to obtain lithium diisopropylamine.

A 0.45 ml (5 mmole) of isobutyronitrile (Tokyo Kasei Co., Ltd.) was dissolved in 5 ml of THF, and the mixture was chilled to −78° C. under nitrogen atmosphere. Thereto was slowly added dropwise lithium diisopropylamine obtained above. The reaction mixture was stirred at −78° C. for 10 minutes and then heated to 0° C. Thereto was added dropwise a solution of 2.223 g (5 mmole) of diphenylbismuthanyl bromide prepared in Preparation Example 3 in 5 ml of THF.

Thereafter the mixture was stirred for one hour while heated to room temperature. The reaction mixture was washed with saturated aqueous solution of NaCl being bubbled by nitrogen gas, and dried by adding anhydrous magnesium sulfate. After filtrated with glass filter and THF was removed in a vacuum, the reaction mixture was recrystallized from diethyl ether at −30° C., giving 0.593 g (1.38 mmol, yield 28%) of light yellow needle crystals.

$^1$H-NMR and $^{13}$C-NMR revealed that the product was the desired one.

$^1$H-NMR (400 MHz, DMSO-d$_6$) 1.86 (s, 6H, CH$_3$), 7.38 (tt, J=1.2 Hz, J=7.4 Hz, 2H, Aromatic H), 7.54 (dt, J=1.2 Hz, J=7.0 Hz, 4H, AromaticH), 7.91 (dd, J=1.2 Hz, J=8.0 Hz, Aromatic H)

$^{13}$C-NMR (100 MHz, DMSO-d$_6$) 24.76 (CH$_3$), 27.43 (Bi—C, quaternary carbon), 127.81 (CN), 128.14 (Aromatic carbon), 130.45 (Aromatic carbon), 136.44 (Aromatic carbon), 164.84 (Bi—C, Aromatic carbon)

Example 4

Preparation of (Dimethylbismuthanyl-Methyl)Benzene

A 40 ml (40 mmole) of 1.0 M solution of benzyl magnesium chloride in diethyl ether was cooled to 0° C., and thereto was added dropwise a solution of 10.2 g (32.1 mmole) of dimethylbismuthanyl bromide prepared in Preparation Example 2 in 20 ml of THF (45 minutes). The reaction mixture was further stirred at 0° C. for 2 hours qnd hexane was added. The supernatant liquid was extracted, concentrated and distilled in a vacuum, giving 3.5 g (yield 32.8%) of a yellow liquid product. b.p. 67-76° C./0.7 mmHg. $^1$H-NMR revealed that the product was the desired one.

$^1$H-NMR (300 MHz, C$_6$D$_6$) 0.85 (s, 6H, BiMe$_2$), 2.87 (s, 2H, CH$_2$), 6.8 (m, 5H, C$_6$H$_5$)

Examples 5 to 16

Preparation of Polystyrene

Along with styrene (Sigma-Aldrich Japan K.K.), methyl 2-dimethylbismuthanyl-2-methylpropionate (Bi initiator) prepared in Example 1, Di Compound and azo type polymerization initiator were placed into a glove box with the inside air replaced by nitrogen, and the reactions were carried out with the ratio and the reaction conditions (time and temperature) as shown in Tables 1a and 1b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain polystyrene.

GPC analysis with reference to the molecular weight of an authentic sample of polystyrene was given in Table 1b.

TABLE 1a

| | monomer (mmol) | Bi initiator (mmol) | Di Compound (mmol) | | azo initiator (mmol) | | |
|---|---|---|---|---|---|---|---|
| | | | ditelluride | distibine | AIBN | ACHN | ADVN |
| Ex. 5 | 10 | 0.1 | | | | | |
| Ex. 6 | 10 | 0.1 | | | 0.025 | | |
| Ex. 7 | 10 | 0.1 | | | 0.025 | | |
| Ex. 8 | 10 | 0.1 | | | 0.05 | | |
| Ex. 9 | 20 | 0.1 | | | | | |
| Ex. 10 | 20 | 0.1 | | | | | 0.002 |
| Ex. 11 | 20 | 0.1 | | 0.05 | | | |
| Ex. 12 | 50 | 0.1 | | | | | |
| Ex. 13 | 50 | 0.1 | | | | | |
| Ex. 14 | 100 | 0.1 | | | | | |
| Ex. 15 | 10 | 0.02 | | | 0.05 | | |
| Ex. 16 | 10 | 0.01 | | | 0.05 | | |

TABLE 1b

| | solvent (ml) | | | reaction condition | | yield | | |
|---|---|---|---|---|---|---|---|---|
| | DMF | THF | toluene | (° C.) | (h) | (%) | Mn | PD |
| Ex. 5 | | | | 100 | 3 | 96 | 10,500 | 1.07 |
| Ex. 6 | | | | 60 | 17 | 76 | 7,500 | 1.08 |
| Ex. 7 | | | | 60 | 29 | 95 | 9,000 | 1.08 |
| Ex. 8 | | | | 60 | 20 | 87 | 10,000 | 1.17 |
| Ex. 9 | | | 2.5 | 100 | 20 | 81 | 25,800 | 1.19 |
| Ex. 10 | | | | 80 | 72 | 85 | 16,300 | 1.22 |
| Ex. 11 | | | | 100 | 12 | 96 | 31,600 | 1.08 |
| Ex. 12 | | | | 100 | 8 | 94 | 52,900 | 1.13 |
| Ex. 13 | 1 | | | 100 | 72 | 85 | 34,000 | 1.15 |
| Ex. 14 | | | | 100 | 16 | 86 | 80,700 | 1.22 |
| Ex. 15 | | | | 60 | 20 | 50 | 83,700 | 1.35 |
| Ex. 16 | | | | 60 | 20 | 41 | 150,500 | 1.49 |

Examples 17 to 20

Preparation of Poly(N-Butyl Acrylate)

Along with n-butyl acrylate (Sigma-Aldrich Japan K.K.), methyl 2-dimethylbismuthanyl-2-methylpropionate (Bi initiator) prepared in Example 1 and 2,2'-azobis-isobutyronitrile (same as above) were placed into a glove box with the inside air replaced by nitrogen, and the reactions were carried out with the ratio and the reaction conditions (time and temperature) as shown in Tables 2a and 2b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(n-butyl acrylate).

GPC analysis with reference to the molecular weight of an authentic sample of poly(methyl methacrylate) was given in Table 2b. In Example 19 only, an authentic sample of polystyrene was used.

TABLE 2a

| | monomer (mmol) | Bi initiator (mmol) | Di Compound (mmol) | | azo initiator (mmol) | | |
|---|---|---|---|---|---|---|---|
| | | | ditelluride | distibine | AIBN | ACHN | ADVN |
| Ex. 17 | 5 | 0.05 | | | | | |
| Ex. 18 | 10 | 0.1 | | | 0.025 | | |
| Ex. 19 | 10 | 0.1 | | | 0.05 | | |
| Ex. 20 | 50 | 0.1 | | | 0.02 | | |

TABLE 2b

| | solvent (ml) | | | reaction condition | | yield | | |
|---|---|---|---|---|---|---|---|---|
| | DMF | THF | toluene | (° C.) | (h) | (%) | Mn | PD |
| Ex. 17 | | | | 100 | 6 | 78 | 10,300 | 1.11 |
| Ex. 18 | | | | 60 | 1 | 93 | 11,200 | 1.09 |
| Ex. 19 | | | | 60 | 6 | 99 | 15,900 | 1.11 |
| Ex. 20 | | | | 60 | 8 | 95 | 52,200 | 1.17 |

Examples 21 to 41

Preparation of Poly(Methyl Methacrylate)

Along with methyl methacrylate (Mitsubishi Gas Chemical Company, Inc.), methyl 2-dimethylbismuthanyl-2-methylpropionate (Bi initiator) prepared in Example 1, Di Compound and azo type polymerization initiator were placed into a glove box with the inside air replaced by nitrogen, and the reactions were carried out with the ratio and the reaction conditions (time and temperature) as shown in Tables 3a and 3b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(methyl methacrylate).

GPC analysis with reference to the molecular weight of an authentic sample of poly(methyl methacrylate) was given in Table 3b. In Examples 25 and 41, an authentic sample of polystyrene was used.

TABLE 3a

| | monomer (mmol) | Bi initiator (mmol) | Di Compound (mmol) | | azo initiator (mmol) | | |
|---|---|---|---|---|---|---|---|
| | | | ditelluride | distibine | AIBN | ACHN | ADVN |
| Ex. 21 | 5 | 0.05 | | | | | |
| Ex. 22 | 10 | 0.1 | | | | | |
| Ex. 23 | 10 | 0.1 | | | 0.005 | | |
| Ex. 24 | 10 | 0.1 | | | 0.025 | | |
| Ex. 25 | 10 | 0.1 | | | 0.05 | | |
| Ex. 26 | 20 | 0.2 | 0.1 | | | | |
| Ex. 27 | 20 | 0.2 | 0.1 | | 0.1 | | |
| Ex. 28 | 20 | 0.2 | 0.1 | | | 0.1 | |
| Ex. 29 | 20 | 0.2 | 0.1 | | | | 0.1 |
| Ex. 30 | 20 | 0.1 | | | | | |
| Ex. 31 | 20 | 0.1 | | 0.01 | | | |
| Ex. 32 | 20 | 0.1 | 0.05 | | 0.02 | | |
| Ex. 33 | 20 | 0.1 | | 0.05 | 0.02 | | |
| Ex. 34 | 50 | 0.1 | | | | | |
| Ex. 35 | 20 | 0.04 | 0.02 | | | | |
| Ex. 36 | 50 | 0.1 | 0.05 | | | | |
| Ex. 37 | 50 | 0.1 | | 0.05 | | | |
| Ex. 38 | 20 | 0.04 | 0.02 | | 0.05 | | |
| Ex. 39 | 50 | 0.1 | 0.05 | | 0.02 | | |
| Ex. 40 | 50 | 0.1 | | 0.05 | 0.02 | | |
| Ex. 41 | 83.2 | 0.1 | | | 0.05 | | |

TABLE 3b

| | solvent (ml) | | | reaction condition | | yield | | |
|---|---|---|---|---|---|---|---|---|
| | DMF | THF | toluene | (° C.) | (h) | (%) | Mn | PD |
| Ex. 21 | | | | 100 | 3 | 79 | 9,100 | 1.13 |
| Ex. 22 | 1 | | | 100 | 10 | 95 | 52,100 | 1.14 |
| Ex. 23 | | | | 60 | 5 | 94 | 15,600 | 1.24 |
| Ex. 24 | | | | 60 | 4 | 88 | 8,200 | 1.31 |
| Ex. 25 | | | | 60 | 5 | 94 | 15,600 | 1.24 |
| Ex. 26 | | | | 90 | 10 | 95 | 11,300 | 1.13 |
| Ex. 27 | | | | 60 | 10 | 89 | 10,700 | 1.12 |
| Ex. 28 | | | | 60 | 10 | 92 | 10,200 | 1.14 |
| Ex. 29 | | | | 40 | 10 | 94 | 10,200 | 1.18 |
| Ex. 30 | | | | 100 | 3 | 93 | 18,600 | 1.10 |
| Ex. 31 | | | | 100 | 3 | 93 | 19,300 | 1.07 |
| Ex. 32 | | | | 60 | 12 | 91 | 17,900 | 1.18 |
| Ex. 33 | | | | 60 | 12 | 91 | 17,100 | 1.14 |
| Ex. 34 | | | | 100 | 4 | 93 | 54,300 | 1.11 |
| Ex. 35 | | | | 90 | 10 | 92 | 43,900 | 1.23 |
| Ex. 36 | | | | 100 | 6 | 91 | 42,400 | 1.20 |
| Ex. 37 | | | | 100 | 6 | 88 | 42,100 | 1.14 |
| Ex. 38 | | | | 60 | 10 | 91 | 40,600 | 1.17 |
| Ex. 39 | | | | 60 | 12 | 90 | 40,900 | 1.21 |
| Ex. 40 | | | | 60 | 12 | 90 | 38,000 | 1.18 |
| Ex. 41 | | | | 60 | 18 | 88 | 87,500 | 1.13 |

Examples 42 to 44

Preparation of poly(1-vinyl-2-pyrrolidone)

Along with 1-vinyl-2-pyrrolidone (Wako Pure Chemical Ind. Ltd.), methyl 2-dimethylbismuthanyl-2-methylpropionate (Bi initiator) prepared in Example 1 and 2,2'-azobis-isobutyronitrile (same as above) were placed into a glove box with the inside air replaced by nitrogen, and the reactions were carried out with the ratio and the reaction conditions (time and temperature) as shown in Tables 4a and 4b. After the completion of the reaction, the reaction mixture was dissolved in 10 ml of tetrahydrofuran, and the solution was then poured into 200 ml of hexane which was being stirred. The resulting polymer precipitate was collected by suction filtration and dried to obtain poly(1-vinyl-2-pyrrolidone).

GPC analysis with reference to the molecular weight of an authentic sample of poly(methyl methacrylate) was given in Table 4b.

TABLE 4a

| | monomer (mmol) | Bi initiator (mmol) | Di Compound (mmol) | | azo initiator (mmol) | | |
|---|---|---|---|---|---|---|---|
| | | | ditelluride | distibine | AIBN | ACHN | ADVN |
| Ex. 42 | 10 | 0.1 | | | 0.02 | | |
| Ex. 43 | 10 | 0.1 | | | 0.025 | | |
| Ex. 44 | 50 | 0.1 | | | 0.02 | | |

TABLE 4b

| | solvent (ml) | | | reaction condition | | yield | | |
|---|---|---|---|---|---|---|---|---|
| | DMF | THF | toluene | (° C.) | (h) | (%) | Mn | PD |
| Ex. 42 | | | | 60 | 1 | 100 | 9,500 | 1.06 |
| Ex. 43 | | | | 60 | 0.5 | 94 | 11,300 | 1.14 |
| Ex. 44 | | | | 60 | 2 | 100 | 60,000 | 1.12 |

Examples 45 to 49

Preparation of Poly(N-Isopropylacrylamide)

Along with N-isopropylacrylamide (Wako Pure Chemical Ind. Ltd.), methyl 2-dimethylbismuthanyl-2-methylpropionate (Bi initiator) prepared in Example 1 and 2,2'-azobis-isobutyronitrile (same as above) were placed into a glove box with the inside air replaced by nitrogen, and the reactions were carried out with the ratio and the reaction conditions (time and temperature) as shown in Tables 5a and 5b. After the completion of the reaction, the reaction mixture was dissolved in 10 ml of tetrahydrofuran, and the solution was then poured into 200 ml of hexane which was being stirred. The resulting polymer precipitate was collected by suction filtration and dried to obtain poly(N-isopropylacrylamide).

GPC analysis with reference to the molecular weight of an authentic sample of poly(methyl methacrylate) was given in Table 5b.

TABLE 5a

| | monomer (mmol) | Bi initiator (mmol) | Di Compound (mmol) | | azo initiator (mmol) | | |
|---|---|---|---|---|---|---|---|
| | | | ditelluride | distibine | AIBN | ACHN | ADVN |
| Ex. 45 | 10 | 0.1 | | | 0.02 | | |
| Ex. 46 | 10 | 0.1 | | | 0.025 | | |
| Ex. 47 | 50 | 0.1 | | | 0.02 | | |
| Ex. 48 | 50 | 0.1 | | | 0.02 | | |
| Ex. 49 | 100 | 0.1 | | | 0.02 | | |

TABLE 5b

| | solvent (ml) | | | reaction condition | | yield | | |
|---|---|---|---|---|---|---|---|---|
| | DMF | THF | toluene | (° C.) | (h) | (%) | Mn | PD |
| Ex. 45 | | | | 60 | 2 | 83 | 8,000 | 1.04 |
| Ex. 46 | 1 | | | 60 | 6 | 99 | 15,900 | 1.07 |
| Ex. 47 | | | | 60 | 8 | 94 | 62,000 | 1.10 |

TABLE 5b-continued

| | solvent (ml) | | | reaction condition | | yield | | |
|---|---|---|---|---|---|---|---|---|
| | DMF | THF | toluene | (° C.) | (h) | (%) | Mn | PD |
| Ex. 48 | 1 | | | 100 | 8 | 94 | 62,000 | 1.10 |
| Ex. 49 | 1 | | | 100 | 8 | 93 | 178,000 | 1.36 |

Example 50

Preparation of Polyacrylonitrile

Along with 0.5 g (10 mmole) of acrylonitrile (Wako Pure Chemical Ind. Ltd.), 34.0 mg (0.10 mmole) of methyl 2-dimethylbismuthanyl-2-methylpropionate (Bi initiator) prepared in Example 1, 4.1 mg (0.025 mmole) of 2,2'-azobis-isobutyronitrile (same as above) and 1 ml of DMF were placed into a glove box with the inside air replaced by nitrogen, followed by stirring at 60° C. for 6 hours. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain 0.52 g (yield 99%) of polyacrylonitrile.

GPC analysis with reference to the molecular weight of an authentic sample of poly(methyl methacrylate) revealed Mn=17100 and PD=1.18.

Example 51

Preparation of Poly(Acrylic Acid)

Along with 0.7 g (10 mmole) of acrylic acid (Sigma-Aldrich Japan K.K.), 34.0 mg (0.1 mmole) of methyl 2-dimethylbismuthanyl-2-methylpropionate (Bi initiator) prepared in Example 1, 8.2 mg (0.05 mmole) of 2,2'-azobis-isobutyronitrile (same as above) and 0.69 ml of tetrahydrofuran were placed into a glove box with the inside air replaced by nitrogen, followed by stirring at 60° C. for 5 hours. After the completion of the reaction, NMR analysis revealed the polymerization degree was 100%. The remained monomer and solvent were removed to obtain 0.66 g (yield 94.3%) of poly(acrylic acid).

Molecular weight distribution analysis was carried out after the carboxylic acid was converted to the corresponding methyl ester. GPC analysis with reference to the molecular weight of an authentic sample of polystyrene revealed Mn=17900 and PD=1.42.

Example 52

Preparation of Poly(Methacrylic Acid)

Along with 0.86 g (10 mmole) of methacrylic acid (Sigma-Aldrich Japan K.K.), 34.0 mg (0.10 mmole) of methyl 2-dimethylbismuthanyl-2-methylpropionate (Bi initiator) prepared in Example 1, 8.2 mg (0.05 mmole) of 2,2'-azobis-isobutyronitrile (same as above) and 2.5 ml of toluene were placed into a glove box with the inside air replaced by nitrogen, followed by stirring at 60° C. for 20 hours. After the completion of the reaction, the remained monomer and solvent were removed to obtain poly(methacrylic acid) (yield 99%).

Molecular weight distribution analysis was carried out after the carboxylic acid was converted to the corresponding methyl ester. GPC analysis with reference to the molecular weight of an authentic sample of poly(methyl methacrylate) revealed Mn=12500 and PD=1.15.

Examples 53 to 54

Preparation of Polystyrene

Along with styrene (same as above) and 2-methyl-2-(dimethylbismuthanyl)propionitrile (Bi initiator) prepared in Example 2 were placed into a glove box with the inside air replaced by nitrogen, and the reactions were carried out with the ratio and the reaction conditions (time and temperature) as shown in Tables 6a and 6b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain polystyrene.

GPC analysis with reference to the molecular weight of an authentic sample of polystyrene was given in Table 6b.

TABLE 6a

|  | monomer (mmol) | Bi initiator (mmol) | Di Compound (mmol) | | azo initiator (mmol) | | |
|---|---|---|---|---|---|---|---|
|  |  |  | ditelluride | distibine | AIBN | ACHN | ADVN |
| Ex. 53 | 10 | 0.1 |  |  |  |  |  |
| Ex. 54 | 50 | 0.1 |  |  |  |  |  |

TABLE 6b

|  | solvent (ml) | | | reaction condition | | yield | | |
|---|---|---|---|---|---|---|---|---|
|  | DMF | THF | toluene | (° C.) | (h) | (%) | Mn | PD |
| Ex. 53 |  |  | 100 | 3 | 95 | 9,000 | 1.17 |
| Ex. 54 |  |  | 100 | 12 | 91 | 28,300 | 1.23 |

Examples 55 to 56

Preparation of Poly(N-Butyl Acrylate)

Along with n-butyl acrylate (Sigma-Aldrich Japan K.K.), 2-methyl-2-(dimethylbismuthanyl)propionitrile (Bi initiator) prepared in Example 2 and 2,2'-azobis-isobutyronitrile (same as above) were placed into a glove box with the inside air replaced by nitrogen, and the reactions were carried out with the ratio and the reaction conditions (time and temperature) as shown in Tables 7a and 7b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(n-butyl acrylate).

GPC analysis with reference to the molecular weight of an authentic sample of poly(methyl methacrylate) was given in Table 7b.

TABLE 7a

| | monomer (mmol) | Bi initiator (mmol) | Di Compound (mmol) ditelluride | distibine | azo initiator (mmol) AIBN | ACHN | ADVN |
|---|---|---|---|---|---|---|---|
| Ex. 55 | 10 | 0.1 | | | 0.02 | | |
| Ex. 56 | 50 | 0.1 | | | 0.02 | | |

TABLE 7b

| | solvent (ml) DMF | THF | toluene | reaction condition (°C.) | (h) | yield (%) | Mn | PD |
|---|---|---|---|---|---|---|---|---|
| Ex. 55 | | | | 60 | 1.5 | 95 | 15,300 | 1.06 |
| Ex. 56 | | | | 60 | 3 | 82 | 64,900 | 1.08 |

Examples 57 to 58

Preparation of Poly(Methyl Methacrylate)

Along with methyl methacrylate (Mitsubishi Gas Chemical Company, Inc.) and 2-methyl-2-(dimethylbismuthanyl)-propionitrile (Bi initiator) prepared in Example 2 were placed into a glove box with the inside air replaced by nitrogen, and the reactions were carried out with the ratio and the reaction conditions (time and temperature) as shown in Tables 8a and 8b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(methyl methacrylate).

GPC analysis with reference to the molecular weight of an authentic sample of poly(methyl methacrylate) was given in Table 8b.

TABLE 8a

| | monomer (mmol) | Bi initiator (mmol) | Di Compound (mmol) ditelluride | distibine | azo initiator (mmol) AIBN | ACHN | ADVN |
|---|---|---|---|---|---|---|---|
| Ex. 57 | 10 | 0.1 | | | | | |
| Ex. 58 | 50 | 0.1 | | | | | |

TABLE 8b

| | solvent (ml) DMF | THF | toluene | reaction condition (°C.) | (h) | yield (%) | Mn | PD |
|---|---|---|---|---|---|---|---|---|
| Ex. 57 | | | | 100 | 3 | 93 | 11,000 | 1.21 |
| Ex. 58 | | | | 100 | 4 | 89 | 51,200 | 1.23 |

Example 59

Preparation of poly(1-vinyl-2-pyrrolidone)

Along with 1.1 g (10 mmole) of 1-vinyl-2-pyrrolidone (same as above), 31.0 mg (0.10 mmole) of 2-methyl-2-(dimethylbismuthanyl)propionitrile (Bi initiator) prepared in Example 2 and 3.28 mg (0.02 mmole) of 2,2'-azobis-isobutyronitrile (same as above) were placed into a glove box with the inside air replaced by nitrogen, followed by stirring at 60° C. for 1 hour. After the completion of the reaction, the reaction mixture was dissolved in 10 ml of tetrahydrofuran, and the solution was then poured into 200 ml of hexane which was being stirred. The resulting polymer precipitate was collected by suction filtration and dried to obtain poly(1-vinyl-2-pyrrolidone) (yield 87%).

GPC analysis with reference to the molecular weight of an authentic sample of poly(methyl methacrylate) revealed Mn=6300 and PD=1.20.

Example 60

Preparation of Poly(N-Isopropylacrylamide)

Along with 1.10 g (10 mmole) of N-isopropylacrylamide (same as above), 31.0 mg (0.10 mmole) of 2-methyl-2-(dimethylbismuthanyl)propionitrile (Bi initiator) prepared in Example 2, 3.28 mg (0.02 mmole) of 2,2'-azobis-isobutyronitrile (same as above) and 1 ml of DMF were placed into a glove box with the inside air replaced by nitrogen, followed by stirring at 60° C. for 2 hours. After the completion of the reaction, the reaction mixture was dissolved in 10 ml of tetrahydrofuran, and the solution was then poured into 200 ml of hexane which was being stirred. The resulting polymer precipitate was collected by suction filtration and dried to obtain poly(N-isopropylacrylamide) (yield 100%).

GPC analysis with reference to the molecular weight of an authentic sample of poly(methyl methacrylate) revealed Mn=13700 and PD=1.13.

Example 61

Preparation of Polystyrene

Along with styrene (same as above) and 2-methyl-2-(diphenylbismuthanyl)propionitrile (Bi initiator) prepared in Example 3 were placed into a glove box with the inside air replaced by nitrogen, and the reactions were carried out with the ratio and the reaction conditions (time and temperature) as shown in Tables 9a and 9b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain polystyrene.

GPC analysis with reference to the molecular weight of an authentic sample of polystyrene was given in Table 9b.

TABLE 9a

|  | monomer (mmol) | Bi initiator (mmol) | Di Compound (mmol) | | azo initiator (mmol) | | |
|---|---|---|---|---|---|---|---|
|  |  |  | ditelluride | distibine | AIBN | ACHN | ADVN |
| Ex. 61 | 10 | 0.1 |  |  |  |  |  |

TABLE 9b

|  | solvent (ml) | | | reaction condition | | yield | | |
|---|---|---|---|---|---|---|---|---|
|  | DMF | THF | toluene | (° C.) | (h) | (%) | Mn | PD |
| Ex. 61 |  |  |  | 100 | 3 | 95 | 25,600 | 1.17 |

Examples 62 to 63

Preparation of Poly(N-Butyl Acrylate)

Along with n-butyl acrylate (Sigma-Aldrich Japan K.K.), 2-methyl-2-(diphenylbismuthanyl)propionitrile (Bi initiator) prepared in Example 3 and 2,2'-azobis-isobutyronitrile (same as above) were placed into a glove box with the inside air replaced by nitrogen, and the reactions were carried out with the ratio and the reaction conditions (time and temperature) as shown in Tables 10a and 10b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(n-butyl acrylate).

GPC analysis with reference to the molecular weight of an authentic sample of poly(methyl methacrylate) was given in Table 10b.

TABLE 10a

|  | monomer (mmol) | Bi initiator (mmol) | Di Compound (mmol) | | azo initiator (mmol) | | |
|---|---|---|---|---|---|---|---|
|  |  |  | ditelluride | distibine | AIBN | ACHN | ADVN |
| Ex. 62 | 10 | 0.1 |  |  | 0.02 |  |  |
| Ex. 63 | 50 | 0.1 |  |  | 0.02 |  |  |

TABLE 10b

| | solvent (ml) | | | reaction condition | | yield | | |
|---|---|---|---|---|---|---|---|---|
| | DMF | THF | toluene | (° C.) | (h) | (%) | Mn | PD |
| Ex. 62 | | | | 60 | 3 | 98 | 13,500 | 1.13 |
| Ex. 63 | | | | 60 | 5 | 98 | 56,300 | 1.14 |

Examples 64 to 65

Preparation of Poly(Methyl Methacrylate)

Along with methyl methacrylate (Mitsubishi Gas Chemical Company, Inc.) and 2-methyl-2-(diphenylbismuthanyl)-propionitrile (Bi initiator) prepared in Example 3 were placed into a glove box with the inside air replaced by nitrogen, and the reactions were carried out with the ratio and the reaction conditions (time and temperature) as shown in Tables 11a and 11b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(methyl methacrylate).

GPC analysis with reference to the molecular weight of an authentic sample of poly(methyl methacrylate) was given in Table 11b.

TABLE 11a

| | | Bi initiator | Di Compound (mmol) | | azo initiator (mmol) | | |
|---|---|---|---|---|---|---|---|
| | monomer (mmol) | (mmol) | ditelluride | distibine | AIBN | ACHN | ADVN |
| Ex. 64 | 10 | 0.1 | | | | | |
| Ex. 65 | 50 | 0.1 | | | | | |

TABLE 11b

| | solvent (ml) | | | reaction condition | | yield | | |
|---|---|---|---|---|---|---|---|---|
| | DMF | THF | toluene | (° C.) | (h) | (%) | Mn | PD |
| Ex. 64 | | | | 100 | 1 | 96 | 13,900 | 1.20 |
| Ex. 65 | | | | 100 | 2 | 86 | 47,600 | 1.30 |

Example 66

Preparation of poly(1-vinyl-2-pyrrolidone)

Along with 1.1 g (10 mmole) of 1-vinyl-2-pyrrolidone (same as above), 43.0 mg (0.10 mmole) of 2-methyl-2-(diphenylbismuthanyl)propionitrile (Bi initiator) prepared in Example 3 and 3.28 mg (0.02 mmole) of 2,2'-azobis-isobutyronitrile (same as above) were placed into a glove box with the inside air replaced by nitrogen, followed by stirring at 60° C. for 2 hours. After the completion of the reaction, the reaction mixture was dissolved in 10 ml of tetrahydrofuran, and the solution was then poured into 200 ml of hexane which was being stirred. The resulting polymer precipitate was collected by suction filtration and dried to obtain poly(1-vinyl-2-pyrrolidone) (yield 85%).

GPC analysis with reference to the molecular weight of an authentic sample of poly(methyl methacrylate) revealed Mn=9800 and PD=1.23.

Example 67

Preparation of Poly(N-Isopropylacrylamide)

Along with 1.10 g (10 mmole) of N-isopropylacrylamide (same as above), 43.0 mg (0.10 mmole) of 2-methyl-2-(diphenylbismuthanyl)propionitrile (Bi initiator) prepared in Example 3 and 3.28 mg (0.02 mmole) of 2,2'-azobis-isobutyronitrile (same as above) were placed into a glove box with the inside air replaced by nitrogen, followed by stirring at 100° C. for 3 hours. After the completion of the reaction, the reaction mixture was dissolved in 10 ml of tetrahydrofuran, and the solution was then poured into 200 ml of hexane which was being stirred. The resulting polymer precipitate was collected by suction filtration and dried to obtain poly(N-isopropylacrylamide) (yield 90%).

GPC analysis with reference to the molecular weight of an authentic sample of poly(methyl methacrylate) revealed Mn=13000 and PD=1.31.

Examples 68 to 75

Preparation of Poly(Methyl Methacrylate)

Along with methyl methacrylate (same as above), (dimethylbismuthanyl-methyl)benzene (Bi initiator) prepared in Example 4 and azo type polymerization initiator were placed into a glove box with the inside air replaced by nitrogen, and the reactions were carried out with the ratio and the reaction conditions (time and temperature) as shown in Tables 12a and 12b. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain poly(methyl methacrylate).

GPC analysis with reference to the molecular weight of an authentic sample of poly(methyl methacrylate) was given in Table 12b.

TABLE 12a

| | monomer (mmol) | Bi initiator (mmol) | Di Compound (mmol) | | azo initiator (mmol) | | |
|---|---|---|---|---|---|---|---|
| | | | ditelluride | distibine | AIBN | ACHN | ADVN |
| Ex. 68 | 28 | 0.28 | | | | | |
| Ex. 69 | 28 | 0.14 | | | | | |
| Ex. 70 | 28 | 0.056 | | | | | |
| Ex. 71 | 28 | 0.028 | | | | | |
| Ex. 72 | 28 | 0.014 | | | | | |
| Ex. 73 | 10 | 0.1 | | | 0.05 | | |
| Ex. 74 | 10 | 0.1 | | | | | 0.05 |
| Ex. 75 | 10 | 0.05 | | | 0.025 | | |

TABLE 12b

| | solvent (ml) | | | reaction condition | | yield | | |
|---|---|---|---|---|---|---|---|---|
| | DMF | THF | toluene | (° C.) | (h) | (%) | Mn | PD |
| Ex. 68 | | | | 90 | 14 | 98 | 12,300 | 1.20 |
| Ex. 69 | | | | 90 | 14 | 94 | 18,000 | 1.43 |
| Ex. 70 | | | | 90 | 21 | 88 | 37,700 | 1.16 |
| Ex. 71 | | | | 90 | 19 | 87 | 56,000 | 1.29 |
| Ex. 72 | | | | 90 | 27 | 88 | 100,100 | 1.30 |
| Ex. 73 | | 1 | | 60 | 24 | 80 | 10,100 | 1.16 |
| Ex. 74 | | 1 | | 50 | 24 | 78 | 9,900 | 1.17 |
| Ex. 75 | | 1 | | 60 | 24 | 90 | 16,000 | 1.19 |

Example 76

Preparation of poly(methyl methacrylate)-polystyrene Random Copolymer

Along with 1.0 g (10 mmole) of styrene (same as above), 1.0 g (10 mmole) of methyl methacrylate (same as above) and 7.0 mg (0.02 mmole) of methyl 2-dimethylbismuthanyl-2-methylpropionate (Bi initiator) prepared in Example 1 were placed into a glove box with the inside air replaced by nitrogen, followed by stirring at 100° C. for 10 hours. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain 1.43 g (yield 71.6%) of poly(styrene-r-methyl methacrylate) random copolymer.

GPC analysis with reference to the molecular weight of an authentic sample of polystyrene revealed Mn=115400 and PD=1.43.

Example 77

Preparation of Poly(N-Isopropylacrylamide)-Poly(N-isopropylmethacrylamide) Random Copolymer Along with 0.57 g (5 mmole) of N-isopropylacrylamide (same as above), 0.64 g (5 mmole) of N-isopropyl-methacrylamide (Wako Pure Chemical Ind. Ltd.), 34.0 mg (0.10 mmole) of methyl 2-dimethylbismuthanyl-2-methylpropionate (Bi initiator) prepared in Example 1, 3.3 mg (0.02 mmole) of 2,2'-azobis-isobutyronitrile (same as above) and 1 ml of DMF were placed into a glove box with the inside air replaced by nitrogen, followed by stirring at 60° C. for 24 hours. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain 1.12 g (yield 93%) of poly(N-isopropylacrylamide-r-N-isopropylmethacrylamide) random copolymer.

GPC analysis with reference to the molecular weight of an authentic sample of polystyrene revealed Mn=17000 and PD=1.37.

Example 78

Stirred in a glove box having its inside air replaced by nitrogen at 60° C. for 22 hours were 351 mg (1.5 mmole) of an adamantane monomer MADM, 556 mg (2.5 mmole) a norbornene monomer NBLM, 59.8 mg (0.18 mmole) of (dimethylbismuthanyl-methyl)benzene prepared in Example 4, 3.0 mg (0.02 mmole) of 2,2'-azobis(isobutyronitrile) and 1.5 ml of tetrahydrofuran. NMR analysis revealed the polymerization degree was 96.7%. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain 0.72 g (yield 79.5%) of poly(MADM-r-NBLM).

GPC analysis with reference to the molecular weight of an authentic sample of polystyrene revealed Mn=4100 and PD=1.38.

Example 79

Preparation of Poly(Methyl Methacrylate)-Polystyrene Diblock Polymer

Along with 0.5 g (5.0 mmole) of methyl methacrylate (same as above), 8.5 mg (0.025 mmole) of methyl 2-dimethylbismuthanyl-2-methylpropionate (Bi initiator) prepared in Example 1 and 2.1 mg (0.125 mmole) of 2,2'-azobis(isobutyronitrile) (same as above) were placed into a glove box with the inside air replaced by nitrogen, followed by stirring at 60° C. for 18 hours. NMR analysis revealed the polymerization degree was 96%. GPC analysis with reference to the molecular weight of an authentic sample of polystyrene revealed Mn=26900 and PD=1.18.

To the poly(methyl methacrylate) obtained above (initiator which is used as macroinitiator) was added 2.0 g (19.2 mmole) of styrene (same as above), followed by stirring at 100° C. for 30 hours. NMR analysis revealed the polymerization degree was 93.1%. After the completion of the reaction, the reaction mixture was dissolved in 10 ml of tetrahydrofuran, and the solution was then poured into 200 ml of methanol which was being stirred. The resulting polymer precipitate was collected by suction filtration and dried to obtain 2.12 g (yield 85%) of poly(methyl methacrylate)-polystyrene diblock polymer GPC analysis with reference to the molecular weight of an authentic sample of polystyrene revealed Mn=204300 and PD=1.39.

Example 80

Preparation of Polystyrene Macroinitiator

Along with 1.04 g (10 mmole) of styrene (same as above) and 34.0 mg (0.10 mmole) of methyl 2-dimethylbismuthanyl-2-methylpropionate (Bi initiator) prepared in Example 1 were placed into a glove box with the inside air replaced by nitrogen, followed by stirring at 100° C. for 6 hours. After the completion of the reaction, the reaction mixture was dissolved in 10 ml of chloroform, and the solution was then poured into 200 ml of methanol which was being stirred. The resulting polymer precipitate was collected by suction filtration and dried to obtain polystyrene macroinitiator (yield 93%).

GPC analysis with reference to the molecular weight of an authentic sample of polystyrene revealed Mn=10900 and PD=1.10.

Example 81

Preparation of poly(styrene-b-1-vinyl-2-pyrrolidone)

Along with 48.4 mg (0.44 mmole) of 1-vinyl-2-pyrrolidone (same as above), 0.41 mg (0.044 mmole) of polystyrene macroinitiator prepared in Example 80, 3.28 mg (0.02 mmole) of 2,2'-azobis-isobutyronitrile (same as above) and 1.5 ml of DMF were placed into a glove box with the inside air replaced by nitrogen, followed by stirring at 60° C. for 18 hours. After the completion of the reaction, the reaction mixture was dissolved in 5 ml of chloroform, and the solution was then poured into 300 ml of diethyl ether which was being stirred. The resulting polymer precipitate was collected by suction filtration and dried to obtain a block copolymer of poly(styrene-b-1-vinyl-2-pyrrolidone) (yield 93%).

GPC analysis with reference to the molecular weight of an authentic sample of polystyrene revealed Mn=32800 and PD=1.28.

INDUSTRIAL APPLICABILITY

The invention provides an organobismuth compound useful as a living radical polymerization initiator which realizes precision control of molecular weights and molecular weight distributions (PD=Mw/Mn) under mild conditions, processes for preparing the compound, processes for preparing polymers using the compound, and the polymers. The living radical polymers obtained by the polymerization process of the invention readily permit conversion of terminal groups to other functional groups, are useful for preparing macromonomers and useful as crosslinking sites and are usable as compatibilizing agents and as materials for block polymers. Further, the present process using organobismuth compound is superior in safety.

The present polymer can be used suitably for resists for use in manufacturing semiconductor devices, etc.

The invention claimed is:

1. An organobismuth compound represented by the formula (1)

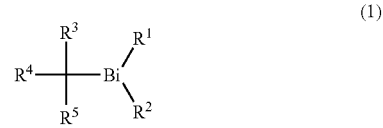

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, amido, oxycarbonyl or cyano, provided that $R^3$ and $R^4$ are not hydrogen atom simultaneously.

2. A process for preparing an organobismuth compound of the formula (1) of claim 1 comprising reacting a compound of the formula (3), and a compound of the formula (4) or (5)

(wherein $R^1$ and $R^2$ are as defined above, and Z is a halogen atom or alkali metal)

(wherein $R^3$, $R^4$ and $R^5$ are as defined above, and X is a halogen atom)

(wherein $R^3$, $R^4$ and $R^5$ are as defined above).

3. A living radical polymerization initiator of the formula (2)

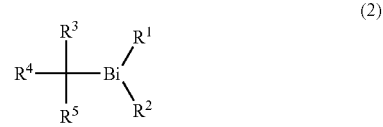

wherein $R^1$ and $R^2$ are $C_1$-$C_8$ alkyl, aryl, substituted aryl or an aromatic heterocyclic group, $R^3$ and $R^4$ are each a hydrogen atom or $C_1$-$C_8$ alkyl, and $R^5$ is aryl, substituted aryl, an aromatic heterocyclic group, acyl, amido, oxycarbonyl or cyano.

4. A process for producing a living radical polymer wherein a vinyl monomer is polymerized with use of a living radical polymerization initiator of the formula (2) of claim 3.

5. A process for producing a living radical polymer wherein a vinyl monomer is polymerized with use of a living radical polymerization initiator of the formula (2) of claim 3 and an azo type polymerization initiator.

6. A living radical polymer which is obtainable by subjecting a vinyl monomer to polymerization with use of a living radical polymerization initiator of the formula (2) of claim 3.

7. A living radical polymer which is obtainable by subjecting a vinyl monomer to polymerization with use of a living radical polymerization initiator of the formula (2) of claim 3 and an azo type polymerization initiator.

8. A mixture of a living radical polymerization initiator of the formula (2) of claim 3 and an azo type polymerization initiator.

9. A process for producing a random copolymer wherein at least two vinyl monomers are polymerized with use of a living radical polymerization initiator of the formula (2) of claim 3.

10. A process for producing a random copolymer wherein at least two vinyl monomers are polymerized with use of a living radical polymerization initiator of the formula (2) of claim 3 and an azo type polymerization initiator.

11. A random copolymer which is obtainable by subjecting at least two vinyl monomers to polymerization with use of a living radical polymerization initiator of the formula (2) of claim 3.

12. A random copolymer which is obtainable by subjecting at least two vinyl monomers to polymerization with use of a living radical polymerization initiator of the formula (2) of claim 3 and an azo type polymerization initiator.

13. A macro living radical polymerization initiator which is obtainable by subjecting a vinyl monomer to polymerization with use of a living radical polymerization initiator of the formula (2) of claim 3.

14. A macro living radical polymerization initiator which is obtainable by subjecting a vinyl monomer to polymerization with use of a living radical polymerization initiator of the formula (2) of claim 3 and an azo type polymerization initiator.

15. A process for producing a block copolymer wherein a vinyl monomer is polymerized with use of a macro living radical polymerization initiator of claim 13.

16. A process for producing a block copolymer wherein a vinyl monomer is polymerized with use of a macro living radical polymerization initiator of claim 14.

17. A block copolymer which is obtainable by subjecting a vinyl monomer to polymerization with use of a macro living radical polymerization initiator of claim 13.

18. A block copolymer which is obtainable by subjecting a vinyl monomer to polymerization with use of a macro living radical polymerization initiator of claim 14.

19. A process for producing a living radical polymer wherein a vinyl monomer is polymerized with use of a mixture of a living radical polymerization initiator of the formula (2) of claim 3, and at least one compound selected from ditelluride compound, distibine compound and dibismuthine compound.

20. A process for producing a living radical polymer wherein a vinyl monomer is polymerized with use of a mixture of a living radical polymerization initiator of the formula (2) of claim 3, an azo type polymerization initiator, and at least one compound selected from ditelluride compound, distibine compound and dibismuthine compound.

21. A living radical polymer which is obtainable by subjecting a vinyl monomer to polymerization with use of a mixture of a living radical polymerization initiator of the formula (2) of claim 3, and at least one compound selected from ditelluride compound, distibine compound and dibismuthine compound.

22. A living radical polymer which is obtainable by subjecting a vinyl monomer to polymerization with use of a mixture of a living radical polymerization initiator of the formula (2) of claim 3, an azo type polymerization initiator, and at least one compound selected from ditelluride compound, distibine compound and dibismuthine compound.

23. A mixture of a living radical polymerization initiator of the formula (2) of claim 3, and at least one compound selected from ditelluride compound, distibine compound and dibismuthine compound.

24. A mixture of a living radical polymerization initiator of the formula (2) of claim 3, an azo type polymerization initiator, and at least one compound selected from ditelluride compound, distibine compound and dibismuthine compound.

25. A process for producing a random copolymer wherein at least two vinyl monomers are polymerized with use of a mixture of a living radical polymerization initiator of the formula (2) of claim 3, and at least one compound selected from ditelluride compound, distibine compound and dibismuthine compound.

26. A process for producing a random copolymer wherein at least two vinyl monomers are polymerized with use of a mixture of a living radical polymerization initiator of the formula (2) of claim 3, an azo type polymerization initiator, and at least one compound selected from ditelluride compound, distibine compound and dibismuthine compound.

27. A random copolymer which is obtainable by subjecting at least two vinyl monomers to polymerization with use of a mixture of a living radical polymerization initiator of the formula (2) of claim 3, and at least one compound selected from ditelluride compound, distibine compound and dibismuthine compound.

28. A random copolymer which is obtainable by subjecting at least two vinyl monomers to polymerization with use of a mixture of a living radical polymerization initiator of the formula (2) of claim 3, an azo type polymerization initiator, and at least one compound selected from ditelluride compound, distibine compound and dibismuthine compound.

29. A macro living radical polymerization initiator which is obtainable by subjecting a vinyl monomer to polymerization with use of a mixture of a living radical polymerization initiator of the formula (2) of claim 3, and at least one compound selected from ditelluride compound, distibine compound and dibismuthine compound.

30. A macro living radical polymerization initiator which is obtainable by subjecting a vinyl monomer to polymerization with use of a mixture of a living radical polymerization initiator of the formula (2) of claim 3, an azo type polymerization initiator, and at least one compound selected from ditelluride compound, distibine compound and dibismuthine compound.

31. A process for producing a block copolymer wherein a vinyl monomer is polymerized with use of a macro living radical polymerization initiator of claim 29.

32. A process for producing a block copolymer wherein a vinyl monomer is polymerized with use of a macro living radical polymerization initiator of claim 30.

33. A block copolymer which is obtainable by subjecting a vinyl monomer to polymerization with use of a macro living radical polymerization initiator of claim 29.

34. A block copolymer which is obtainable by subjecting a vinyl monomer to polymerization with use of a macro living radical polymerization initiator of claim 30.

35. A process for producing a resin containing an acid-dissociable group wherein a vinyl monomer is polymerized with use of one of the following (a) to (d),
- (a) a living radical polymerization initiator of the formula (2) of claim 3,
- (b) a mixture of a living radical polymerization initiator of the formula (2), and an azo type polymerization initiator,
- (c) a mixture of a living radical polymerization initiator of the formula (2), and at least one compound selected from ditelluride compound, distibine compound and dibismuthine compound, and
- (d) a mixture of a living radical polymerization initiator of the formula (2), an azo type polymerization initiator, and at least one compound selected from ditelluride compound, distibine compound and dibismuthine compound.

36. A resin containing an acid-dissociable group which is obtainable by the process of claim 35.

37. A radiation-sensitive resin composition comprising a resin containing an acid-dissociable group, and a radiation-sensitive acid producing agent, the resin containing an acid-dissociable group being a resin obtained by subjecting a vinyl monomer to polymerization with use of one of the following (a) to (d),
- (a) a living radical polymerization initiator of the formula (2) of claim 3,
- (b) a mixture of a living radical polymerization initiator of the formula (2), and an azo type polymerization initiator,
- (c) a mixture of a living radical polymerization initiator of the formula (2) of claim 3, and at least one compound selected from ditelluride compound, distibine compound and dibismuthine compound, and
- (d) a mixture of a living radical polymerization initiator of the formula (2) of claim 3, an azo type polymerization initiator, and at least one compound selected from ditelluride compound, distibine compound and dibismuthine compound.

* * * * *